United States Patent [19]
Krumdieck et al.

[11] Patent Number: 5,650,389
[45] Date of Patent: Jul. 22, 1997

[54] METHODS FOR THE INHIBITION OF COMPLEMENT ACTIVATION

[75] Inventors: Richard Krumdieck, Birmingham, Ala.; Magnus A. O. Höök, Houston, Tex.; John E. Volanakis, Birmingham, Ala.

[73] Assignee: University of Alabama at Birmingham Research Foundation, Birmingham, Ala.

[21] Appl. No.: 25,357

[22] Filed: Mar. 1, 1993

[51] Int. Cl.$^6$ .......................... A61K 38/00; A61K 35/12
[52] U.S. Cl. ...................................... 514/8; 435/2
[58] Field of Search ........................ 435/2; 514/2, 8; 530/300, 350

[56] References Cited

U.S. PATENT DOCUMENTS

| | | | |
|---|---|---|---|
| 4,990,502 | 2/1991 | Corneau et al. | 514/56 |
| 5,109,114 | 4/1992 | Nicholson-Weller | 530/350 |
| 5,171,674 | 12/1992 | Stevens et al. | 435/69.1 |

OTHER PUBLICATIONS

Bidanset et al., "Binding of the Proteoglycan Dacorin to Collagen Type VI," *The Journal of Biological Chemistry*, 267 (8) :5250–5256, 1992.
Conrad et al.,"Antibodies Against the Predominant Glycosaminoglycan of the Mammalian Cornea, Keratan Sulfate–I," *The Journal of Biological Chemistry*, 257:464–471, 1982.
Cooper, Neil R., "The Classical Complement Pathway: Activation and Regulation of the First Complement Component," *Advances in Immunology*, 37:151–216, 1985.
Fisher et al., "Proteoglycans of Developing Bone," *The Journal of Biological Chemistry*, 258:6588–6594, 1983.
Funderburgh et al., "Arterial Lumican: Properties of a Corneal–Type Keratan Sulfate Proteoglycan from Bovine Aorta," *The Journal of Biological Chemistry*, 266:24773–24777, 1991.
Heinegard et al., "Two Novel Matrix Proteins Isolated from Articular Cartilage Show Wide Distributions among Connective Tissues," *The Journal of Biological Chemistry*, 261:13866–13872, 1986.
Krumdieck et al., "The Proteoglycan Decorin Binds C1q and Inhibits the Activity of the C1 Complex," *The Journal of Immunology*, 149(11):3695–3701, 1992.
Krumdieck et al., "Decorin Binds C1Q and Inhibits the Activity of C1," FASEB Journal, 6(4):A1121, Abstract #1074, 1992.
Nakazawa et al., "Defective Processing of Keratan Sulfate in Macular Corneal Dystrophy," *The Journal of Biological Chemistry*, 259:13751–13757, 1994.
Quigg, R.J., "Inhibition of the Alternative Pathway of Complement by Glomerular Chondroitin Sulphate Proteoglycan," *Immunology*, 76:373–377, 1992.
Schumaker et al., "Activation of the First Componenet of Complement," *Annual Reviews of Immunology*, 5:21–42, 1987.

Vogel et al., "Specific Inhibition of Type I and Type II Collagen Fibrillogenesis by the Small Proteoglycan of Tendon," *Biochemical Journal*, 223:587–597, 1984.
Dialog Search Report dated Dec. 28, 1992 and Dec. 29, 1992.
Silvestry et al. J. Biol. Chem. 256: 7383–7387 (1981).
Scott Biochem. J. 252: 313–323 (1988).
Quigg Kidney Intl. 40: 668–676 (1991).
Quigg, R.J. (1991) "Isolation of a novel complement regulatory factor (GCRF) from glomerular epithelial cells", *Kidney International*, 40:668–676.
Scott, J. E. (1988) "Proteoglycan–fibrillar collagen interactions", *Biochem. J.*, 252:313–323.
Silvestri, L. et al., (1981) "The C1q inhibitor in serum is a chondroitin 4–sulfate proteoglycan", *J. Biol. Chem.*, 256:7383–7387.
PCT Search Report, mailed May 3, 1994.
Lizbfwski et al. in Paul, Raven Press 1993 Fundamental Immunology p. 932.
Almeda et al. J. Biol Chem. 258:785–791 (1983).
Morgan Eur. J. Clin Invest. 24:219–228 (1994).
Kalli et al. Springer Semin Immuno Pathol. 15:417–431 (1994).
Franklin Biochemical Pharmacology 49:267–273 (1995).

*Primary Examiner*—Christina Y. Chan
*Assistant Examiner*—Phillip Gambel
*Attorney, Agent, or Firm*—Benjamin Aaron Adler

[57] ABSTRACT

Decorin, a small collagen-binding dermatan sulfate proteoglycan, is widely distributed as a component of extracellular matrices. Using a solid phase binding assay, the inventors demonstrated that decorin bound C1q at physiologic pH and ionic strength. The interaction did not require divalent cations and was time and temperature dependent reaching equilibrium in 4 hours at 37° C. Binding was specific and saturable with an apparent dissociation constant of $7.6 \times 10^{-9}$M. Decorin was shown to bind pepsin-derived fragments containing the collagenous domain of C1q and collagenase-derived fragments containing the globular domain of C1q. Since these fragments share a short sequence of amino acids, this finding suggests that decorin binds to a region of C1q located near the junction of the two domains. Competition studies using purified preparations of the decorin core protein and the glycosaminoglycan chains showed that only the former inhibited binding of decorin to C1q indicating that the interaction is mediated by the decorin core protein. Decorin was shown to inhibit the hemolytic activity of purified C1 as well as C1 in normal human serum. Approximately 50% inhibition was observed at a decorin concentration of 2 µg/ml. Inhibition was not observed if C1 was bound to antigen-complexed antibody. Furthermore, neither the core protein, nor the glycosaminoglycan chain of decorin inhibited C1 indicating that the intact proteoglycan is necessary for functional activity. These studies therefore demonstrate the usefulness of decorin and related proteoglycans in suppression of complement activation of the immune system.

20 Claims, 11 Drawing Sheets

METHODS FOR THE INHIBITION OF COMPLEMENT ACTIVATION

The government owns rights in the present invention pursuant to grant numbers AI21067, AM27807, AR34614 from the National Institutes of Health.

BACKGROUND OF THE INVENTION

1. Field of the Invention

The present invention relates generally to the field of immunology and more particularly to methods and compositions for inhibiting complement mediated inflammatory reactions.

2. Description of the Related Art

The complement system is a major effector system of host defense against infectious microorganisms. It is composed of more than 30 plasma and membrane proteins which when activated, result in the generation of biologically active peptide fragments and protein complexes which promote acute inflammation, enhance the clearance of microorganisms by host phagocytic cells, and directly kill invading pathogens.

The complement system can be activated via two pathways, an antibody-dependent pathway called the classical pathway and an antibody-independent pathway called the alternative pathway (1,2). Activation of either pathway results in the assembly of enzymes called C3 convertases which cleave complement component C3 at a single peptide bond to form C3a and C3b. Some of the C3b molecules then bind to the C3 convertases changing their substrate specificity such that they now cleave C5 to C5a and C5b. All of the biological activities of the complement system, in turn, are derived from the cleavage products of C3 and C5.

Several cell surface proteins have been described which regulate complement activity and protect cellular elements of host tissues from complement mediated injury. These include membrane cofactor protein (MCP)/CD46, decay accelerating factor (DAF), membrane inhibitor of reactive lysis (MIRL)/CD59, and homologous restriction factor (HRF)/C8-binding protein (18–24).

C1q is a subcomponent of the C1 complex, the first component of the classical pathway of complement activation (25). Certain matrix proteins have been shown to bind C1q including fibronectin (40, 41), laminin (42), and fibrin (43). These interactions are saturable and appear to be specific; however, with the exception of laminin, binding of C1q to these proteins has been demonstrated only under conditions of low ionic strength. Furthermore, the interaction of C1q with these matrix proteins has not been demonstrated to alter the activity of C1, thus, their biological relevance is uncertain.

Though the integrity of the complement system is necessary for effective protection against infectious organisms, when excessively activated or misdirected, complement-mediated inflammation can result in damage to host tissues. For example, complement-mediated inflammation has been demonstrated to produce host tissue damage in animal models of autoimmune diseases such as collagen-induced arthritis (8, 9), myasthenia gravis (10, 11), and membranous nephropathy (12, 13). Complement activation also, in part, mediates the tissue destruction which occurs following myocardial infarction (14, 15) and burn injuries (16, 17).

While advances have been made in our understanding of the regulation of complement-mediated inflammation, there is presently no satisfactory way to inhibit complement activation and protect the host tissues in an autoimmune inflammatory response. There exists a particular need for the identification of substances that are both well tolerated with few side effects that are effective in inhibiting or suppressing complement-mediated immune responses.

SUMMARY OF THE INVENTION

It is an object of the invention to address one or more foregoing or other shortcomings in the prior art through the provision of pharmaceutical compositions having the ability to suppress or dampen inflammation in diseases such as myocardial infarction, thermal injury or certain autoimmune conditions such as immune complex-mediated arthritis, associated with complement-mediated damage to host tissues.

It is a particular object to provide pharmaceutical compositions that effect in vivo or in vitro suppression at physiological pH and ionic strengths, and are composed of an active component that is not foreign to the body.

It is a further object to provide for the development of proteoglycan coatings for bio-materials such as plastic hemodialysis tubing or tubing used to achieve extracorporeal circulation during cardiac surgery, which inhibits the complement response to the introduction of the bio-materials into a human subject.

The present invention is directed to these and other objects, and arises out of the inventors' discovery and demonstration that the proteoglycan decorin has the ability to bind to C1q and suppress or inhibit C1 complex biological activity. In diseases where complement is misdirected or excessively activated resulting in damage to host tissues, it is proposed that this inhibition will suppress one or more of the deleterious effects of antibody-mediated complement activation, such as recruitment and activation of inflammatory cells, vasodilation, and/or direct cell killing via formation of membrane attack complex which is the lytic component system, thereby providing significant advantages over existing therapies and an ideal solution to the problem of complement activation. Moreover, decorin is a naturally occurring proteoglycan found in tissues throughout the body that exhibits good C1 complex inhibition. Decorin may in fact be involved in the natural control of complement activation. Thus, the inventors expect that it will be well tolerated physiologically.

Based upon these observations the inventors propose that other members of the decorin family of proteoglycans, including biglycan, lumican, and perhaps even fibromodulin. These proteoglycans demonstrate homology in the structure of their core proteins which are comprised predominantly of tandemly repeated segments 24 residues in length with leucine residues in conserved positions.

In particular aspects the invention thus concerns pharmaceutical compositions having the ability to suppress C1 complex activity, composed of a therapeutically effective amount of decorin in a condition rendered pharmacologically acceptable. It is contemplated that such compositions may be conveniently provided in a ready-to-use aqueous solution, or a lyophilized form for mixing into solution just prior to use. In either case, one will desire to prepare the decorin agent composition such that the ultimate solution will be physiologically acceptable, e.g., sterile, dispersed in either water, dextrose water, physiological saline or physiologic buffered solutions such as PBS, Hank's balanced salt solutions, Ringer's lactate or a comparable salt in an acceptable buffer at more or less neutral pH.

The source of decorin or related agent is not believed to be particularly critical, and will typically depend on the contemplated application. Where clinical application is contemplated one will desire to employ a decorin species that is matched to the particular species to be treated. Thus, where humans are to be treated or will receive decorin-coated objects, human decorin will be preferred. In the case of in vitro applications, though, such as in assays employing the inhibition of C1 complex as a component or control, the species employed is not believed to be particularly critical.

Isolation from natural sources is one means of obtaining useful quantities. Preferred naturally occurring starting sources include bovine articular cartilage, skin, and bone. Biglycan can be isolated from the same sources. Fibromodulin may be isolated from bovine cartilage and lumican from chick and bovine cartilage and bovine aorta. Human decorin has been cloned and expressed in CHO cells, and may be obtained from such sources. Decorin is obtained from tissues such as these employing published procedures that have been found by the inventors to provide adequately purified material.

Alternatively, it is contemplated that recombinantly produced decorin agents will be equally effective as naturally isolated decorin, so long as it is produced in a host cell that will produce the proteoglycan in a biologically active form. The decorin cDNA has been isolated and characterized, and can be employed to prepare recombinant decorin.

Decorin is found to be optimally active in inhibiting C1 complex activity at concentrations of from 0.2 to 20 ug/ml, and particularly at about 2 to 5 ug/ml. Thus, for direct clinical applications one will typically desire to provide compositions sufficiently concentrated, on the order of 5 mg/ml (which is readily achievable in physiologic buffers), to allow one to administer convenient bolus injections (e.g., of about 1.5 to 3.5 mls.) which will achieve plasma concentrations within the foregoing ranges.

Alternatively, one may choose to administer the decorin composition by slow infusion over periods of time, wherein lower concentrations may be preferred. When administered as a continuous infusion decorin may be dissolved into parenteral solutions, such as D5W, normal saline or Ringer's lactate, all of which are widely used in medical practice for the treatment of a variety of conditions.

In other embodiments, the invention concerns a method for binding a decorin agent to C1q in solution. This application of decorin has usefulness both in vivo applications—this is proposed to be an underlying mechanism of decorin's complement suppression action—and in vitro applications. In in vitro applications, decorin will find particular use as a component of assays for characterization of C1 complex action or even in drug screening assays to identify agents that interact with C1q or the C1 complex. Decorin is bound to C1q simply by providing a C1q solution and adding to such a solution an amount of decorin that is effective to allow binding of the decorin to the C1q, typically an amount that will provide a final concentration of on the order of 0.2 to 20 ug/ml.

In still other embodiments, the invention concerns a method for inhibiting C1 complex activity in solution, again based upon the finding that decorin, and perhaps related compounds, will effectively suppress C1 complex activity. This aspect involves adding to such a solution an amount of decorin that is effective to suppress one or more biological consequences of C1 complex action. As with C1q binding, the inhibition of C1 complex function is observed a final concentrations of about 2 ug/ml are 50% effective at about, and are more or less maximally active at about 10 ug/ml (greater than 90% inhibition). Moreover, decorin is found to be active in the presence of serum. Thus, it is proposed that C1 complex action will be achieved in vivo upon achieving similar concentrations.

The finding that decorin suppresses C1 complex action has indicated to the inventors that decorin will find a variety of applications beyond direct, parenteral administration. For example, the inventors contemplate that decorin will prove useful as a biological coating for implanted medical devices, such as tubings, shunts, catheters, artificial implants, pins, and even electrical implants such as pacemakers. In these embodiments it is contemplated that decorin can be bound actively using coupling techniques involving activation of the biomaterial surface by chemical reagents such as EDC followed by a coupling to amino groups or carboxyl groups on the decorin molecule; or adsorbed to the surface of these biomaterials passively through adsorption onto the surface of the biomaterial.

Coupling of decorin to the biomaterial surface could also be enhanced by using decorin derivatives where the active domains of decorin would be altered through genetic or chemical manipulation to facilitate the coupling. Such procedures may involve introducing a hydrophobic segment in the decorin molecule, or introducing a set of positively charged lysine residues which would facilitate absorption to the biomaterial.

BRIEF DESCRIPTION OF THE DRAWINGS

FIG. 1 shows the saturation binding curve of decorin to C1q.

FIG. 1A shows the binding of [$^{125}$I]decorin to microtiter wells coated with incremental concentrations of C1q, following incubation with solutions containing $5\times10^4$ cpm. Following incubation, unbound decorin was removed and bound decorin (calculated as the amount of decorin bound to wells coated with C1q minus that bound to wells coated with BSA) was measured.

FIG. 1B shows binding of [$^{125}$I] C1q to microtiter wells coated with incremental concentrations of decorin, following incubation with solutions containing $5\times10^4$ cpm. Following incubation, unbound C1q was removed and bound C1q was quantitated as described. Data points represent the mean and standard error of triplicate determinations.

FIG. 2 is a study showing that the binding of [$^{125}$I]decorin to C1q is time dependent. Microtiter wells coated with either C1q (open squares), or with BSA (closed squares) were incubated at 37° C. for various time periods with solutions containing $5\times10^4$ cpm of [$^{125}$I]decorin. At the indicated incubation times, unbound decorin was removed and bound decorin was quantitated. Closed triangles represent binding of decorin to C1q at 0°–4° C. Data points represent the mean and standard error of duplicate determinations.

FIG. 3 shows the inhibition of binding of [$^{125}$I]decorin to solid-phase C1q by NHS and C1q-depleted serum. Microtiter wells coated with C1q were incubated with solutions containing $5\times10^4$ cpm of [$^{125}$I]decorin and incremental concentrations of either NHS (closed squares), or C1q-depleted serum (open squares). Following incubation, unbound material was removed and bound [$^{125}$I]decorin was quantitated, as described. Results are expressed as percent of control samples without inhibitor. Data points represent the mean values obtained in two separate experiments.

FIG. 4A is a saturation assay plot wherein microtiter wells coated with either C1q, or BSA were incubated with solutions containing incremental concentrations of [$^{125}$I]decorin (specific activity ~200,000 cpm/μg). Following incubation, unbound decorin was removed and both bound and unbound decorin were quantitated. Open squares represent decorin bound to C1q, closed squares represent decorin bound to BSA, and closed triangles represent specifically bound decorin. Data points represent the mean and standard error of triplicate determinations.

FIG. 4B is a Scatchard plot of the saturation assay data—The dissociation constant of the decorin-C1q interaction calculated as the negative reciprocal of the slope of the line, was estimated at $7.6 \times 10^{-9}$M.

FIG. 5A compares the binding of decorin to wells coated with either BSA, intact C1q, the collagenous fragments of C1q (C1q-C), or the globular fragments of C1q (C1q-G), following incubation with solutions containing $5 \times 10^4$ cpm of [$^{125}$I]decorin. Following incubation, unbound decorin was removed and bound decorin was quantitated as described. Each bar on the graph represents the mean and standard error of triplicate determinations.

FIG. 5B shows the binding of decorin to wells coated with C1q, following incubation with solutions containing $5 \times 10^4$ cpm of [$^{125}$I]decorin and incremental concentrations of either intact C1q (open squares), C1q-C (open triangles), or C1q-G (closed squares). Following incubation, unbound material was removed and bound [$^{125}$I]decorin was quantitated. Data points represent the mean and standard error of triplicate determinations.

FIG. 6 shows that the binding of [$^{125}$I]decorin to C1q is mediated by the decorin core protein. Wells coated with C1q were incubated with solutions containing $5 \times 10^4$ cpm of [$^{125}$I]decorin and incremental concentrations of either unlabeled intact decorin (open squares), decorin core protein (closed triangles), or GAG chains (closed squares). Following incubation, unbound material was removed and bound [$^{125}$I]decorin was quantitated as described. Data points represent the mean and standard error of triplicate determinations.

FIG. 7 shows the effects of decorin in a C1 fixation assay. Purified C1 was incubated with incremental concentrations of either intact decorin (open squares), decorin core protein (open triangles), or GAG chains (closed squares), residual C1 activity was measured by hemolytic assay. Data points represent the mean of duplicate determinations.

FIG. 8 further shows that superoxide production is inhibited in wells containing decorin at a concentration of 100 mg/ml, and that the degree of inhibition is equal to that observed in wells containing superoxide dismutase at the same concentration.

Figure 1A:
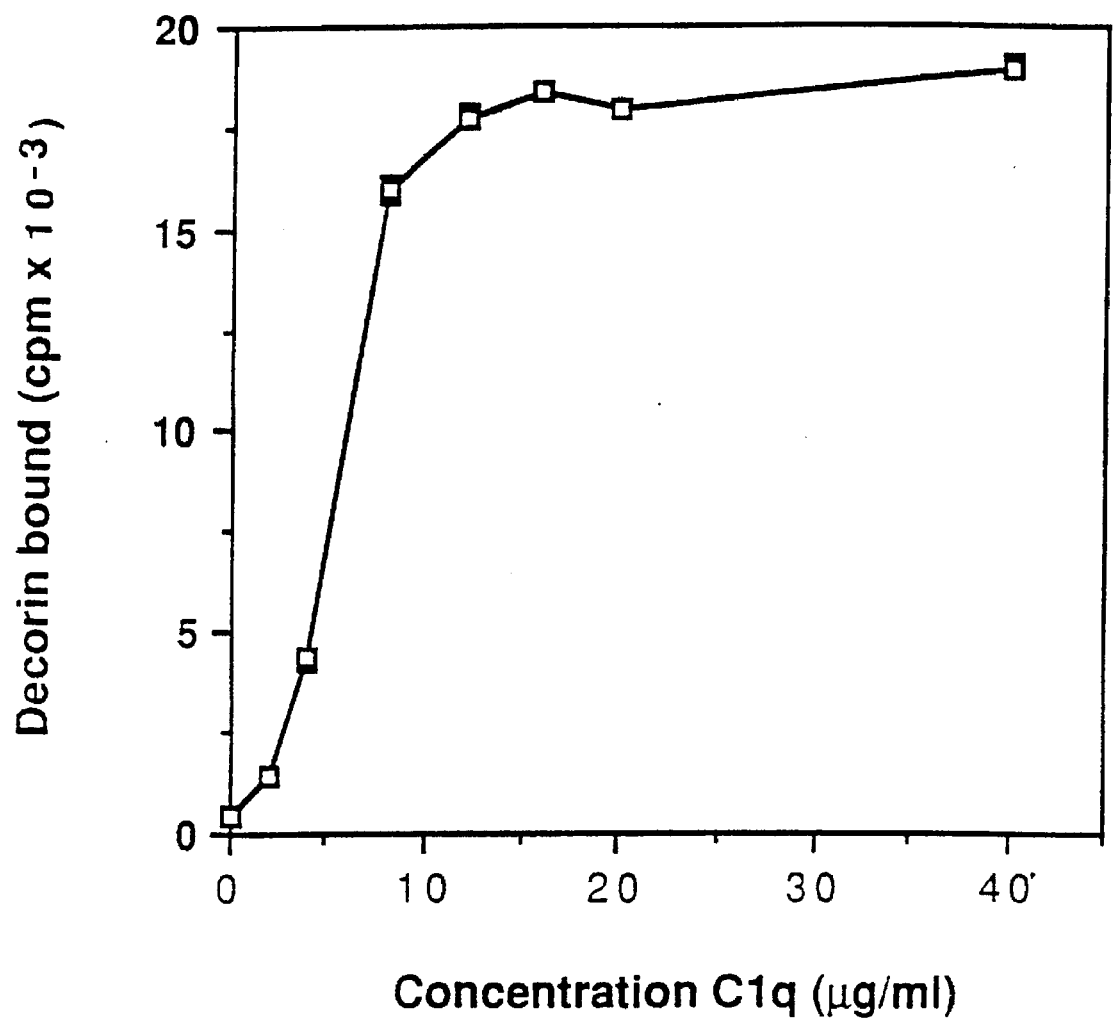

DETAILED DESCRIPTION OF THE INVENTION a. Introduction

The complement system is a major effector system of host defense against infectious microorganisms. It is composed of more than 30 plasma and membrane proteins which when activated, result in the generation of biologically active peptide fragments and protein complexes which promote acute inflammation, enhance the clearance of microorganisms by host phagocytic cells, and directly kill invading pathogens.

The complement system can be activated via two pathways, an antibody-dependent pathway called the classical pathway and an antibody-independent pathway called the alternative pathway (1,2). Activation of either pathway results in the assembly of enzymes called C3 convertases which cleave complement component C3 at a single peptide bond to form C3a and C3b. Some of the C3b molecules then bind to the C3 convertases changing their substrate specificity such that they now cleave C5 to C5a and C5b.

All of the biological activities of the complement system, in turn, are derived from the cleavage products of C3 and C5. C3a and C5a are anaphylatoxins which promote acute inflammation by binding to mast cells and basophils, and triggering the release of inflammatory mediators such as histamine and leukotrienes (3). C5a further promotes acute inflammation by functioning as a chemotaxin for phagocytic leukocytes, and enhancing the secretion of tumor necrosis factor-a and interleukins by these cells (4). C3b (and its cleavage product iC3b), covalently bind to pathogenic organisms and enhance their clearance by host phagocytes (5). C5b serves as a nidus for the formation of a protein complex called the membrane attack complex (MAC) which inserts into the phospholipid bilayer of cellular membranes resulting in the osmotic lysis of susceptible cells (6). The importance of the complement system in host defense is underscored by the observation that genetic deficiencies of many of the complement components result in an increased susceptibility to pyogenic infections (7).

Though the integrity of the complement system is necessary for effective protection against infectious organisms, when excessively activated or misdirected, complement-mediated inflammation can result in damage to host tissues. For example, complement-mediated inflammation has been demonstrated to produce host tissue damage in animal models of autoimmune diseases such as collagen-induced arthritis (8,9), myasthenia gravis (10,11), and membranous nephropathy (12,13). Complement activation also, in part, mediates the tissue destruction which occurs following myocardial infarction (14,15) and burn injuries (16,17).

Several cell surface proteins have been described which regulate complement activity and protect cellular elements of host tissues from complement mediated injury. These proteins include membrane cofactor protein (MCP)/CD46, decay accelerating factor (DAF), membrane inhibitor of reactive lysis (MIRL)/CD59, and homologous restriction factor (HRF)/C8-binding protein. MCP inhibits complement activity by binding C3b and C4b, and acting as a cofactor for their cleavage by the serine protease, factor I (18). Transfection of cell lines with MCP has been demonstrated to protect the transfected cells from complement-mediated lysis (19). DAF also binds C3b and C4b, but rather than functioning as a cofactor for factor I, it inhibits complement activity by preventing the assembly and promoting the dissociation of the C3 convertases of both the classical and alternative pathways (20). MIRL and HRF act at a more distal point in the complement cascade inhibiting the assembly of the membrane attack complex on host cells (21,22). The latter three proteins (DAF, MIRL, and HRF) share a common characteristic: all are inserted into the membranes of host cells via a glycolipid anchor (23). Proteins anchored in this manner are deficient in a fraction of the circulating cells in individuals with paroxysmal nocturnal hemoglobinuria. This deficiency has been causally related to the enhanced susceptibility of the red cells to complement-mediated lysis observed in this disorder (24).

While significant advances have been made concerning the regulation of complement-mediated inflammation by cell surface components of host tissues, very little is known about how extracellular matrix components interact with complement to regulate its activity. We propose that elucidation of mechanisms by which matrix components modulate complement-mediated inflammation would be not only of biological interest, but also may contribute to our understanding of the pathogenesis of diseases associated with complement-mediated damage to host tissues. In addition, this line of investigation may lead to the development of pharmacologic interventions to dampen inflammation in these disorders. To date, most of the research in this area has focused on the interaction of complement component C1q with components of extracellular matrices.

b. Structure and Function of C1q

C1q is a subcomponent of the C1 complex, the first component of the classical pathway of complement activation (25). C1q has a molecular mass of 460 kDa and is composed of six copies of three distinct polypeptide chains designated A, B, and C (26). The three chains are of similar molecular weight (approx. 26 kDa) and overall structure. Beginning close to the amino-terminus, each chain contains a collagen-like sequence (Gly-X-Y) approximately 80 amino acids in length followed by a non-collagen like sequence approximately 136 amino acids in length. One molecule of each of the three chains associate to form the subunits of C1q which contain a collagen triple helix contiguous with a globular domain. Six of these subunits, in turn, associate to form the intact C1q molecule which when viewed by electron microscopy has the appearance of a bouquet of flowers with six peripherally located globular heads connected via fibrillar strands to a central collagenous stalk (27).

In plasma, C1q circulates as a $Ca^{2+}$-dependent complex with two molecules each of the serine protease proenzymes, C1r and C1s (25). C1r and C1s bind to the collagenous domain of C1q in a region close to the globular domain (28,29). The globular domain, in turn, mediates binding of C1 to IgG- and IgM-containing immune complexes (30). Binding to immune complexes induces a conformational change in C1q which results in the autoactivation of C1r (31). C1r then activates C1s followed by the activation of C4 and C2 and the assembly of the C3 convertase of the classical pathway, (Schumaker et al. 1987).

Dissociation of the C1 complex by C1-inhibitor fully exposes the collagenous domain of C1q. This domain has been demonstrated to mediate binding of C1q to several cell types including monocytes (33), B-lymphocytes (33), fibroblasts (34), and neutrophils (33). Binding of C1q to these cells is saturable and specific consistent with a receptor ligand interaction. Furthermore, the interaction of C1q with these cells elicits specific cellular responses. For example, C1q enhances Fc-receptor mediated phagocytosis by monocytes (35), immunoglobulin production by B-lymphocytes (36), and chemotaxis in fibroblasts (37). C1q when immobilized on latex beads (38), or when immobilized on plastic surfaces (39), stimulates oxidative burst in human neutrophils. Monomeric C1q in solution, however, does not elicit this cellular response suggesting that multi-valency of the ligand is required for functional activity.

c. Interaction of C1q with Matrix Proteins

Several matrix proteins have been shown to bind C1q including fibronectin (40,41), laminin (42), and fibrin (43). These interactions are saturable and specific; however, with the exception of laminin, binding of C1q to these proteins has been demonstrated only under conditions of low ionic strength. Furthermore, the interaction of C1q with these matrix proteins has not been demonstrated to alter the activity of C1, thus, their biological relevance is uncertain. Recently, we have been investigating the interaction of C1q with a matrix proteoglycan called decorin.

d. Structure and Function of Decorin

Decorin is a dermatan-sulfate proteoglycan which is widely distributed as an extracellular matrix component of numerous tissues including articular cartilage, bone, skin, adventitia of arterial vessels, connective tissue septae of skeletal and cardiac muscle, and cornea (44,45). The decorin molecule has a Mr of 87,000–120,000 by SDS-PAGE and is composed of a core protein and a single glycosaminoglycan chain (46). The cDNA deduced amino acid sequence of the core protein of human decorin shows that it is composed of 329 amino acids with a Mr 36,319 (47). Seventy percent of the primary structure of the core protein consists of ten tandemly repeated segments 24 amino acid residues in length which contain leucine residues in conserved positions (48). Similar leucine-rich motifs have been detected in other matrix proteoglycans such as biglycan (49), lumican (50), and fibromodulin (51), as well as in several other proteins of diverse origin and function including the leucine-rich glycoprotein of serum (a protein of unknown function) (52), glycoprotein Ib (a platelet membrane receptor for von Willebrand factor) (53), yeast adenylate cyclase (54), and two drosophila proteins, chaoptin and Toll protein (55,56). The leucine-rich motifs of some of these proteins have been postulated to mediate protein-protein (57) and protein-membrane (55) interactions.

Though the biological function of decorin is not known, it has been shown to bind several proteins including fibronectin (58), transforming growth factor-b (TGF-b) (59), and certain types of fibrillar collagens (60,61). Binding is mediated by the decorin core protein and the interaction of decorin with these proteins results in structural, or functional alterations of the bound proteins. For example, decorin inhibits fibroblast attachment to the cell binding domain of fibronectin (62) and the mitogenic activity of TGF-b on CHO cells (59). The interaction of decorin with fibrillar collagen types I and II retards collagen fibrillogenesis in vitro (63).

The inventors discovery that decorin binds to C1q are set forth in detail below, with studies demonstrating that decorin binds C1q at physiologic pH and ionic strength. The interaction is saturable with a dissociation constant of $7.6 \times 10^{-9}$M and is mediated by the decorin core protein which appears to bind C1q in a region close to the junction between the collagenous and globular domains. The inventors have shown further that decorin, when incubated with either purified C1 or C1 in normal human serum, inhibits activation of the classical complement pathway. In addition, preliminary data suggests that decorin also inhibits C1q-mediated superoxide production by neutrophils.

At present, the biological significance of the decorin-C1q interaction is not known. The inventors propose that decorin may modulate complement-mediated inflammation at sites where decorin-containing extracellular matrices are exposed to complement components. Consistent with this hypothesis are the observations that decorin is concentrated at the surfaces of articular cartilage as determined by immunohistochemical studies (44), and that loss of stainable proteoglycans at the articular surface is the earliest histological change observed in rat models of collagen induced arthritis (64,65) suggesting that the surface proteoglycans may serve a protective role. Though this is an interesting possibility, at this time the physiologic significance the binding of decorin to C1q remains uncertain. However, the observation that the interaction occurs at physiologic ionic strength, and results in both the inhibition of C1-initiated complement pathway activation and C1q-mediated superoxide production by neutrophils, suggests that this is a physiologically relevant interaction which merits further study.

e. Preparation of Pharmaceutical Compositions

Aqueous compositions (inocula) of the present invention comprise an effective amount of the decorin family agent dissolved or dispersed in a pharmaceuticaly acceptable aqueous medium. Such compositions are also referred to as inocula. The phrase "pharmaceutically acceptable" refers to molecular entities and compositions that do not produce an allergic or similar untoward reaction when administered to a human.

The preparation of an aqueous composition that contains a protein or proteoglycan as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A proteoglycan can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Figure 1B:
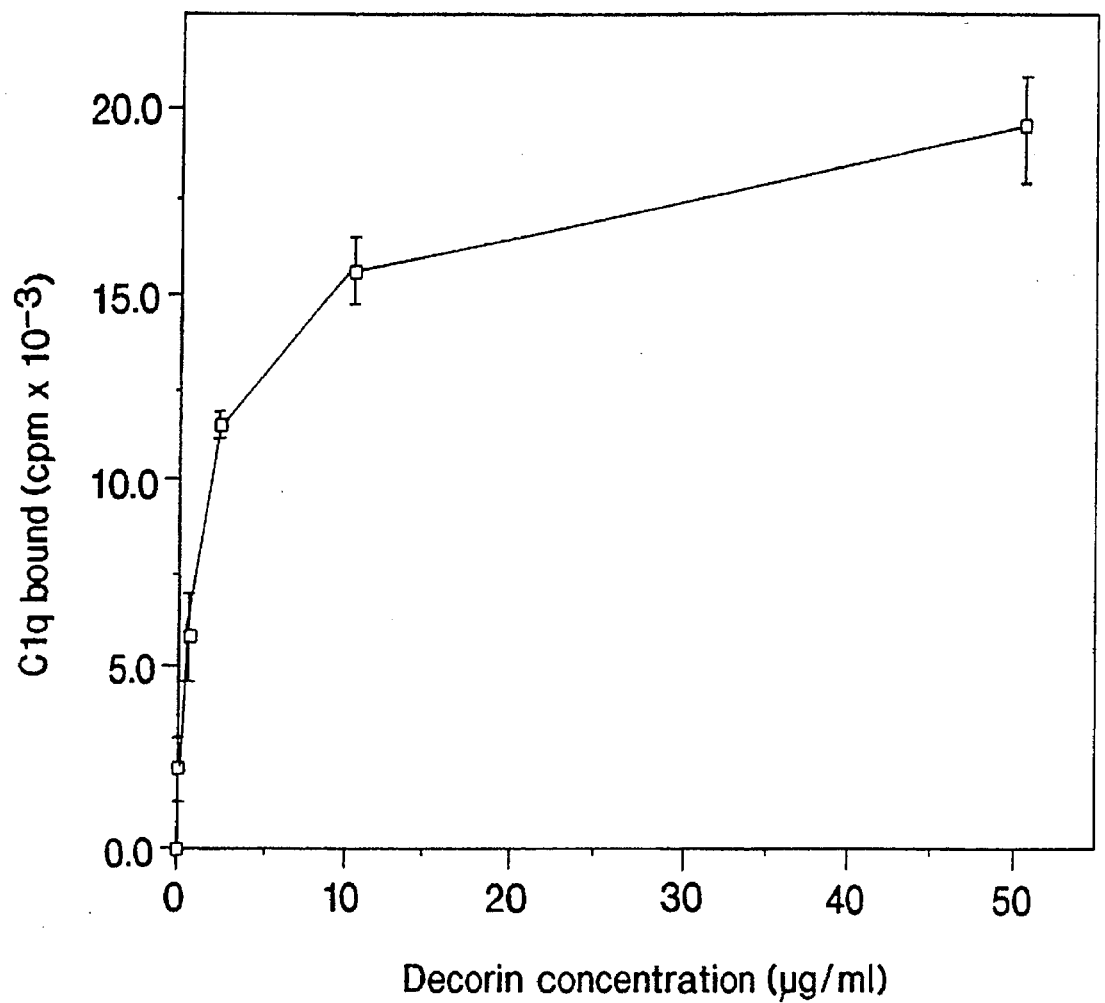

The present example demonstrates methods employed by the inventors to prepare decorin as well as various binding and inhibition studies. Certain studies are presented to demonstrate the binding of decorin to C1q at physiologic pH and ionic strength (FIG. 1). The interaction is saturable with a dissociation constant of $7.6 \times 10^{-9}$M and is mediated by the decorin core protein which appears to bind C1q in a region close to the junction between the collagenous and globular domains. Decorin also inhibits activation of the classical complement pathway when incubated with either purified C1 or C1 in normal human serum. In addition, decorin may inhibit C1q-mediated superoxide production by neutrophils.

MATERIALS AND METHODS

A. Buffers

The buffers employed in the following studies included: PBS (0.137M NaCl, 0.08M $Na_2HPO_4$, 0.015M $KH_2PO_4$, 0.027M KCl, 0.5 mM $MgCl_2$, 0.9 mM $CaCl_2$ adjusted to pH 7.4); $GVB^{++}$ (Veronal-buffered saline (0.142M $NaCl_2$, 5 mM sodium diethylbarbiturate, pH 7.4) containing 0.1% gelatin, 1 mM $MgCl_2$ and 0.15 mM $CaCl_2$); $DGVB^{++}$ contains 63% (w/v) $GVB^{++}$ and 37% of a solution of 5% (w/v) dextrose in water, 0.1% (w/v) gelatin, 1 mM $MgCl_2$ and 0.15 mM $CaCl_2$.

B. Purification of Decorin, Decorin Core Protein and Glycosaminoglycan Chains

Decorin was purified from bovine articular cartilage as previously described, incorporated herein by reference (27). The inventors prepared core protein of decorin by digestion of the intact proteoglycan with chondroitinase ABC according to the manufacturer's instructions. Briefly, 2 ml of a 2 mg/ml solution of decorin in 0.1M Tris-HCl, 0.03M sodium acetate, pH 8.0 were incubated with chondroitinase ABC (0.2 units/mg protein) for 4 hours at 37° C. The core protein was purified by FPLC on a Mono-Q column equilibrated with 0.05M Tris-HCl, 6M urea, 6 mM CHAPS, pH 8.0 and eluted with a 20 ml gradient of 0 to 0.4M NaCl in the equilibration buffer at a flow rate of 0.5 ml/min. One ml fractions were collected and their absorbance was monitored at 280 nm. Three peaks were obtained and the second peak was shown to contain the decorin core protein by SDS-PAGE which yielded a single protein band migrating with an apparent molecular weight of 45,000. Fractions corresponding to the second peak were pooled and dialyzed against PBS. The glycosaminoglycan chains of decorin were prepared as previously described incorporated herein by reference (46).

C. Purification of C1q and Preparation of C1q Fragments

C1q was purified from human plasma as described by Tenner et al (97) and included herein as reference. Purity of the preparations was demonstrated by SDS-PAGE and Western blotting both of which yielded three protein bands with apparent molecular weights of 26,500, 30,500, and 32,000. The concentration of C1q was estimated from its absorbance at 280 nm using an extinction coefficient ($E_{1cm}$) of 6.82 (67).

Proteolytic fragments containing the collagenous domain of C1q were prepared by limited digestion of C1q with pepsin according to the method of Reid and Porter (66) included herein by reference. The pepsin resistant collagenous fragments were purified by FPLC on a Superose-12 gel filtration column as described by Jiang et al (102) included herein by reference. Purity of the preparations was demonstrated by SDS-PAGE and protein concentrations were estimated from absorbance of the samples at 275 nm ($E_{1cm}$=2.1) (105).

Proteolytic fragments containing the globular domain of C1q were prepared by digestion of C1q with collagenase according to the method of Reid and Edmondson (67) included herein by reference. The collagenase resistant globular fragments were purified by FPLC on a Superose-12 column as described by Jiang et al (102) included herein by reference. Purity of the preparations was demonstrated by SDS-PAGE and protein concentrations were estimated from absorbance at 280 nm ($E_{1cm}$=7.0) (67).

D. Iodination of Decorin and C1q

Decorin and C1q were radiolabeled with $Na^{125}I$ using ENZYMOBEADS™ according to the manufacturer's instructions. Labeled protein was separated from free iodine by chromatography on PD-10 columns equilibrated with PBS containing 1% BSA and eluted with PBS. The estimated specific activities of the radiolabeled protein preparations were 1–2×$10^7$ cpm/µg.

E. Solid-Phase Binding Assays

Binding of decorin to C1q was assayed as follows: IMMULON™-2-removawells were coated overnight at 4° C. with 50 µl of C1q (20 µg/ml) in PBS. Unbound material was decanted and non-specific binding sites were blocked by incubating the wells with 1% BSA in PBS for 1 h at room temperature. The wells then were washed with PBS, and 5×$10^4$ cpm of [$^{125}I$]decorin diluted in 100 µl of 0.1% BSA-PBS was added to each well. The mixtures were incubated at 37° C. for 3 to 4 h, and unbound material was removed by washing three times with PBS containing 0.1% BSA and 0.1% Triton-X 100. Wells then were detached, placed in 12×17 mm plastic tubes and radioactivity was quantitated with a gamma counter. Values for nonspecific binding were obtained by measuring the amount of radiolabeled decorin bound to wells coated with 1% BSA-PBS.

In competition assays, radiolabeled decorin was mixed with increasing concentrations of the inhibitor and 100, or 200 µl of the mixtures were added to C1q coated wells. Binding of decorin to C1q was assayed as before. In calculations involving molar concentrations, the following molecular weights were used: C1q 460,000, C1q collagenous fragments 190,000, C1q globular fragments 48,000 (16), and decorin 100,000 (46).

F. Preparation of BSA-anti-BSA Complexes

BSA-anti-BSA complexes were prepared at equivalence by mixing equal volumes of BSA (200 µg/ml) and heat-inactivated rabbit anti-BSA serum as previously described and included herein by reference (99).

G. Hemolytic Assays

1. C4 consumption assay

One hundred microliter aliquots of normal human serum (NHS), diluted 1:5 with GVB$^{++}$,were incubated with 10 µl aliquots of solutions containing incremental concentrations of decorin in GVB$^{++}$, or BSA-anti-BSA complexes for 1 h at 0° C. The mixtures then were incubated 30 min at 30° C. and residual C4 activity was measured according to the method of Gaither et al (68) included herein by reference. Hemolytic units were calculated as described (104), and results were expressed as percent of control samples incubated only with buffer.

2. C1 Fixation Assay

Five hundred microliter aliquots of purified C1, or NHS, diluted with DGVB$^{++}$ to a C1 activity of 1 unit, were incubated with 50 µl aliquots of solutions containing incremental concentrations of decorin, the decorin core protein, or glycosaminoglycan chains for 1 h at 0° C. Following incubation, residual C1 activity was measured as described by Borsos and Rapp (69) included herein by reference.

H. SDS-PAGE and Western Blotting

Analytical SDS-PAGE on 5–15% polyacrylamide gradient gels was carried out as previously described by Laemmli and Favre (76) and included herein by reference. Gels were stained for 30 minutes with solutions of 0.25% Coomasie brilliant blue, 7% acetic acid and 50% methanol and destained with solutions of 10% methanol and 10% acetic acid. Alternatively, gels were silver stained as previously described by Goldman et al (106) and included herein by reference.

For Western blot analysis of C1q, the protein was electrophoresed on polyacrylamide gels under reducing conditions and transferred to nitro-cellulose filters (NYTRAN™, Schleicher & Schuell Inc. Keene, N.H.) by electroblotting (107). Additional protein binding sites were blocked by incubating the filters with 5% non-fat dried milk in Tris buffered saline (10mM Tris-HCl, 150 mM NaCl, pH 7.4) for 2 h at room temperature. Filters then were washed and incubated for 2 h at room temperature with rabbit anti-C1q serum prepared by the inventors. Filters again were washed and incubated 1 h at room temperature with alkaline phosphatase-conjugated goat anti-rabbit IgG (Bio-Rad, Richmond Calif.). Immunoreactive proteins were visualized by developing the filter with BCIP/NBT.

BINDING AND INHIBITION STUDIES

A. Decorin Binding to C1q

A solid-phase binding assay was employed to study the interaction of decorin and C1q. FIG. 1A shows that [$^{125}I$] decorin bound to microtiter wells coated with incremental concentrations of C1q. The amount of decorin bound was proportional to the concentration of the C1q solutions employed to coat the wells and reached a plateau at a concentration of 10 µg/ml. At this concentration approximately 40% of the added radiolabeled decorin was bound, whereas only 1% bound to wells coated with BSA alone.

The inventors also examined whether [$^{125}I$] C1q would bind solid-phase decorin. FIG. 1A shows that radiolabeled C1q bound to wells coated with increasing concentrations of decorin and the amount of C1q bound was proportional to the amount of decorin employed to coat the wells. Addition of 5 mM EDTA did not inhibit binding, indicating that the interaction does not require divalent cations. In addition, it should be noted that these and all subsequent binding studies were carried out in phosphate buffered saline at pH 7.4 indicating that binding of decorin to C1q occurs at physiologic pH and ionic strength.

B. The Kinetics of the Decorin-C1q Interaction

Figure 2:
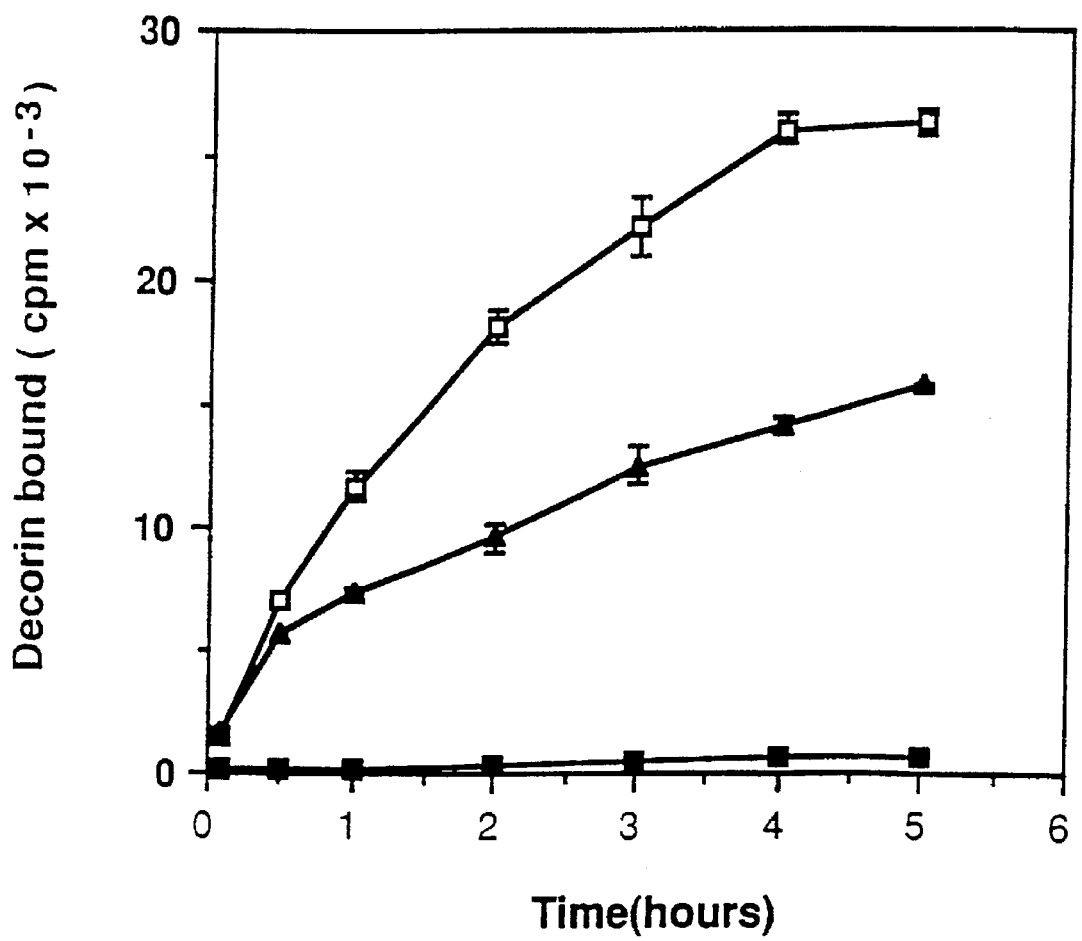

Radiolabeled decorin was added to solid-phase C1q and the mixtures were incubated at 37° C. for various periods of time. Following incubation, unbound material was removed and the amount of radiolabeled decorin remaining bound to the wells was quantitated as in section V, above. FIG. 2 shows that binding of decorin to C1q was time-dependent and reached a maximum in 4 h at 37° C. Binding also was examined at temperatures of 0°–4° C. by immersing the C1q coated microtiter wells in an ice water bath during the assay. As shown in FIG. 2, the amount of decorin bound to C1q at 0°–4° C. was approximately 55% of that observed at 37° C. and maximum binding was not reached over an incubation period of five hours indicating a temperature-dependent binding process.

C. Specificity of the Decorin-C1q Interaction

Figure 3:
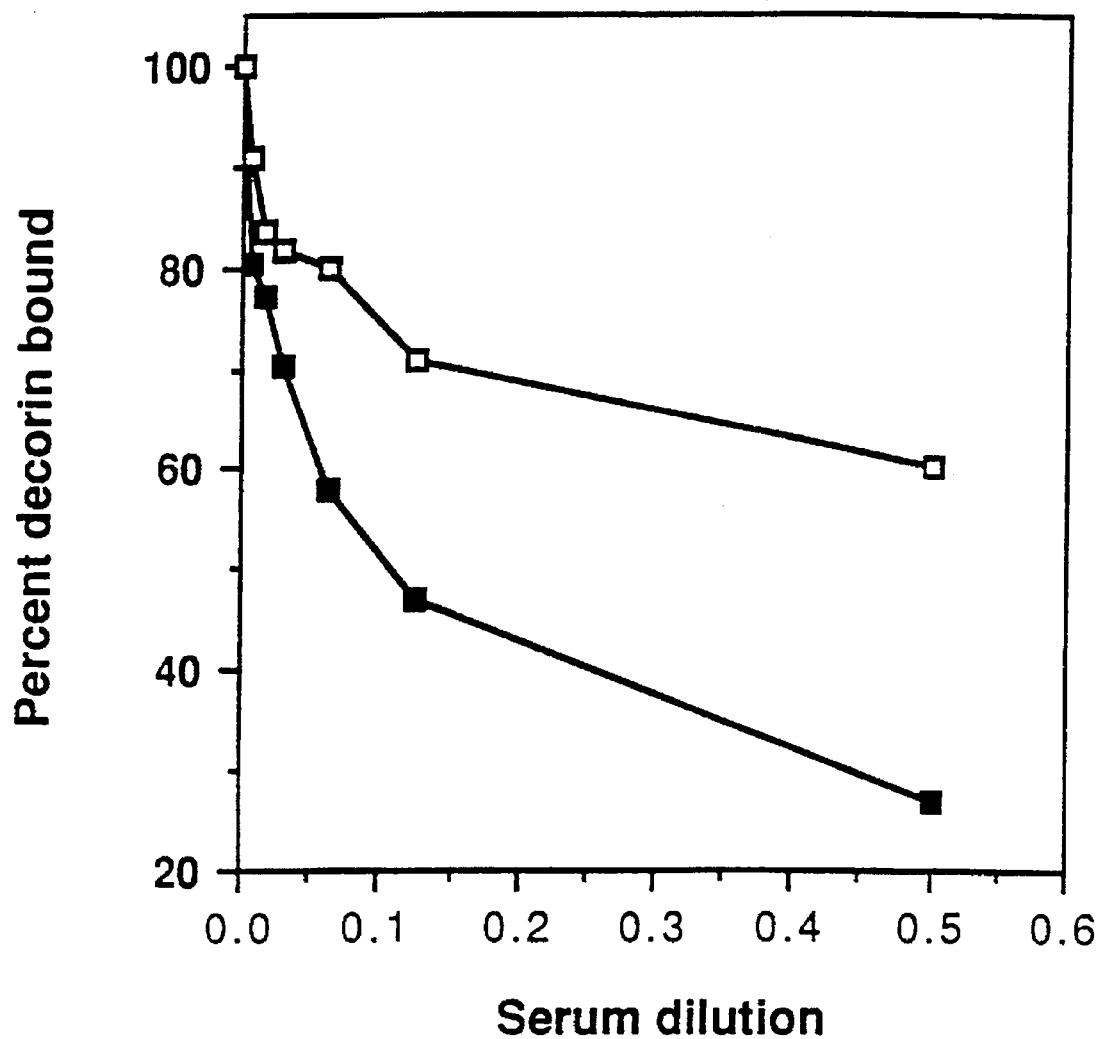

A competition assay was performed by the inventors using either NHS, or C1q-depleted serum as inhibitors of the binding of radiolabeled decorin to solid-phase C1q. FIG. 3 shows that NHS produced a dose-dependent inhibition of the binding of radiolabeled decorin to C1q, whereas C1q-depleted serum only partially inhibited the decorin-C1q interaction. At an inhibitor dilution of 0.5 (obtained by mixing equal volumes of [$^{125}$I]decorin with undiluted serum) NHS inhibited binding of radiolabeled decorin to C1q by 73%, while C1q-depleted serum inhibited binding by only 40%.

D. Saturability of the Decorin-C1q Interaction

Figure 4A:
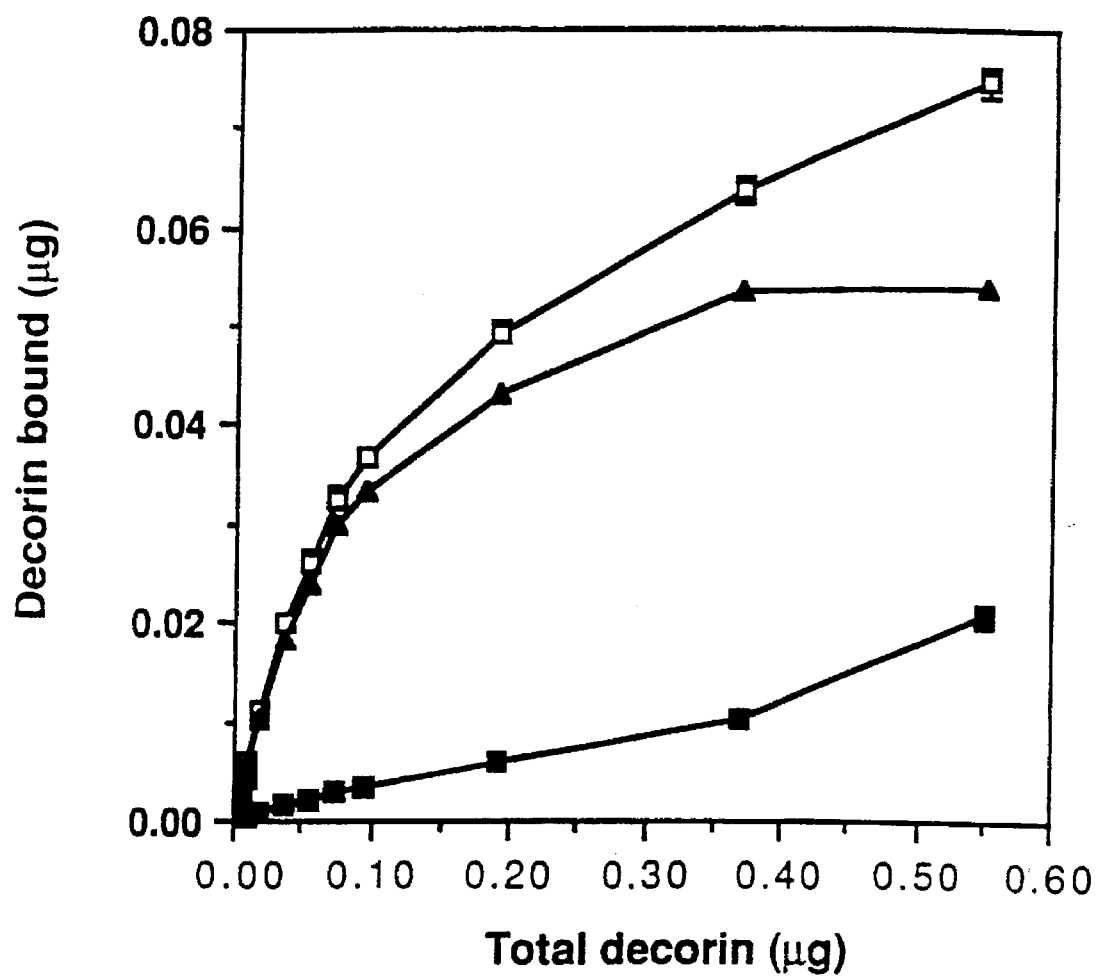
Figure 4B:
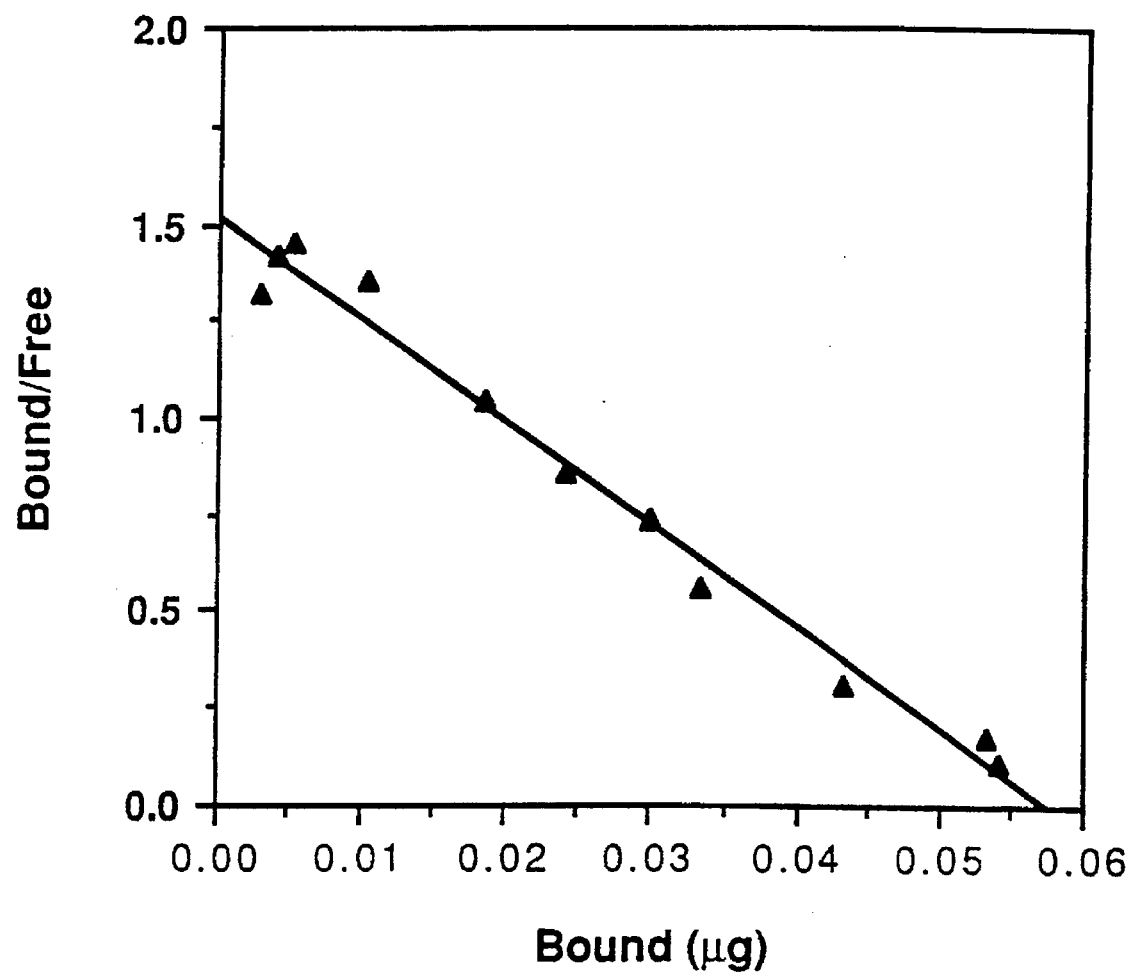

Increasing amounts of radiolabeled decorin (specific activity ~200,000 cpm/µg) were added to wells coated either with C1q, or as a measure for nonspecific binding, with BSA. The mixtures were incubated at 37° C. for 4 h and then bound and unbound decorin were quantitated as described above in section V. FIG. 4A demonstrates that specific binding of decorin to C1q, estimated as the amount of decorin bound to C1q minus that bound to BSA, reached a plateau when more than 0.4 µg of decorin was added to solid-phase C1q indicating that the interaction is saturable. A Scatchard plot (101) of the data produced a straight line (FIG. 4B) indicating the presence of a single class of binding sites. The dissociation constant for the decorin-C1q interaction, calculated as the negative reciprocal of the slope of the line in FIG. 4B, was estimated to be $7.6 \times 10^{-9}$M at pH 7.4 and ionic strength 0.15.

Since application of the method of Scatchard to calculate dissociation constants requires that the binding reaction be reversible (108), we attempted to demonstrate reversibility by displacing C1q-bound radiolabeled decorin with excess unlabeled decorin. The experiment was performed as follows: radiolabeled decorin was added to C1q coated wells and the mixtures were incubated for 1 h at 37° C. Following incubation, unbound radiolabeled decorin was removed by aspiration and 100 µl of solutions containing a 500–1000 fold excess of unlabeled decorin were added. The mixtures again were incubated at 37° C., and at various time points unbound material was removed and bound radiolabeled decorin was quantitated as previously described. Results of this experiment showed no appreciable displacement of radiolabeled decorin over a period of 6 h, a finding consistent with the high affinity of the interaction. Since reversibility was not demonstrated, the dissociation constant calculated from the Scatchard plot should be considered as an apparent value.

E. Localization of the Decorin Binding Site on

Figure 5A:
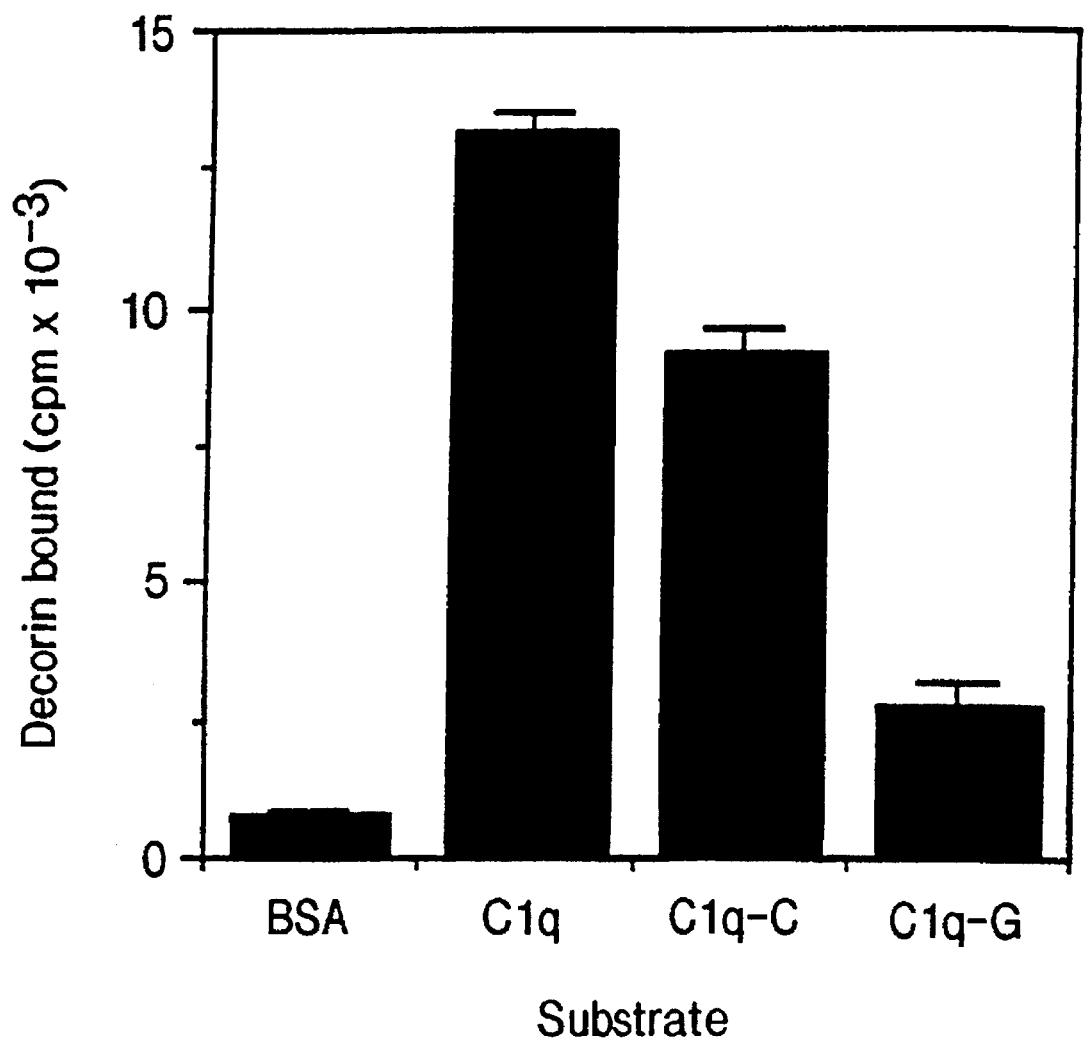

Proteolytic fragments containing either the collagenous or globular domains of C1q were obtained by limited proteolysis of intact C1q with pepsin or collagenase, respectively. Microtiter wells then were coated with 20 mg/ml of intact C1q, the collagenous fragment of C1q (C1q-C), the globular fragment of C1q (C1q-G), or 1% BSA, and binding of [$^{125}$I] decorin was quantitated. FIG. 5A shows that wells coated with C1q-C, or C1q-G bound radiolabeled decorin at levels higher than that bound to wells coated with BSA, but lower than to wells coated with intact C1q. Binding of decorin to C1q-C and to C1q-G was 70% and 21%, respectively of that observed to intact C1q. The differences in the amount of decorin which bound C1q-C and C1q-G may reflect differences in the affinity of decorin for the C1q fragments, or in the amounts of the fragments which bound to the microtiter wells. In order to correct for the latter variable, a competition assay using intact C1q, C1q-C, and C1q-G as fluid-phase inhibitors of the binding of radiolabeled decorin to solid-phase C1q also was performed.

Figure 5B:
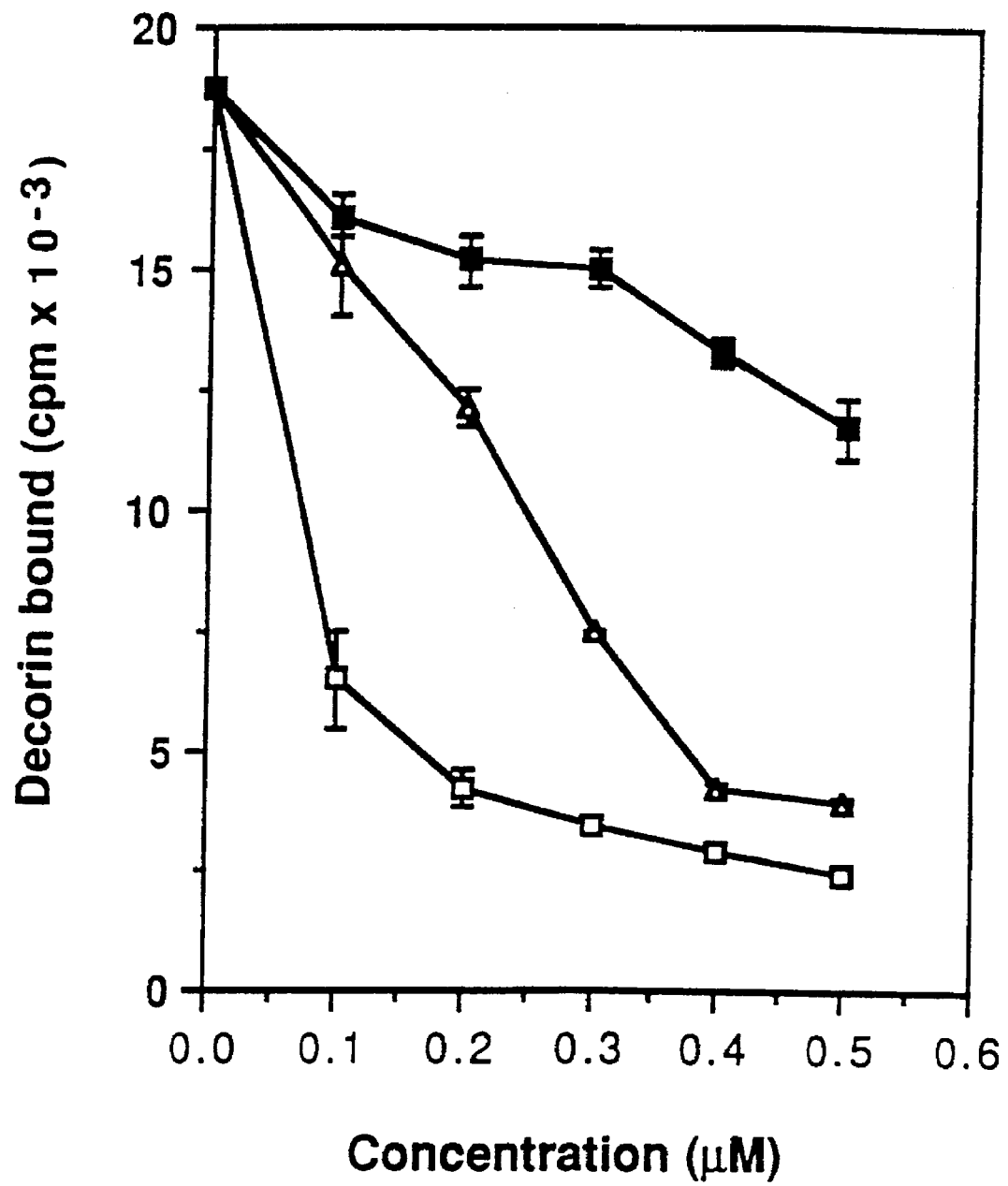

FIG. 5B shows that both intact C1q and C1q-C produced a dose-dependent inhibition of the binding of decorin to solid-phase C1q. C1q-G also inhibited the decorin-C1q interaction, but apparently to a lesser extent. However, since each molecule of C1q and C1q-C contains six identical subunits, while each molecule of C1q-G contains only a single globular head, the inhibition of the decorin-C1q interaction by C1q-G also was tested at an inhibitor concentration of 2.4 µM, equal to six times the molar concentration of C1q which produced near maximal inhibition. At this concentration C1q-G inhibited binding of [$^{125}$I] decorin to C1q by 90%. These data demonstrate that decorin binds to both pepsin-derived collagenous fragments and the collagenase-derived globular fragments of C1q.

F. Localization of the C1q Binding Site on Decorin

Figure 6:
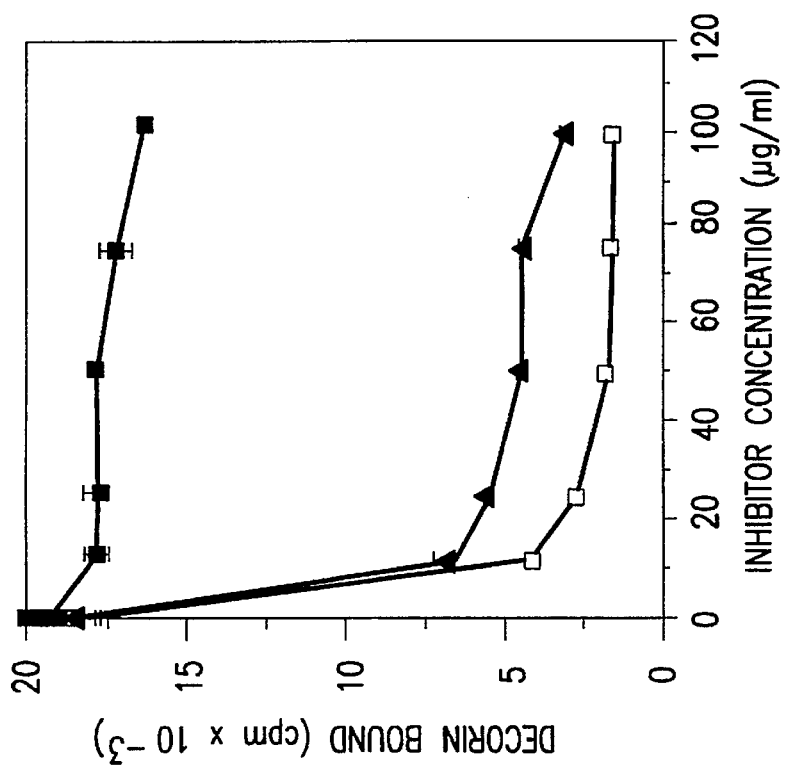

The inventors tested intact decorin, the decorin core protein, and the GAG chain as competitive inhibitors of the binding of [$^{125}$I]decorin to solid-phase C1q. FIG. 6 shows that both intact decorin and the decorin core protein inhibited binding of [$^{125}$I]decorin to C1q, whereas, isolated GAG chains had no inhibitory effect. This demonstrates that binding of decorin to C1q is mediated by the core protein of decorin.

G. Inhibition of C1 by Decorin

The inventors first examined whether decorin would activate C1 in NHS. Activation of C1 was determined indirectly by measuring C4 consumption following incubation of NHS with increasing concentrations of decorin, or as a positive control, BSA-anti-BSA complexes. Decorin (0–0.1 mg/ml) when incubated with NHS did not produce consumption of C4, whereas BSA anti-BSA complexes produced a dose-dependent reduction of C4 activity. Fifty percent C4 consumption was observed at a BSA concentration of 0.08 mg/ml. This result demonstrates that though decorin binds C1q, it does not activate the C1 complex.

Figure 7:
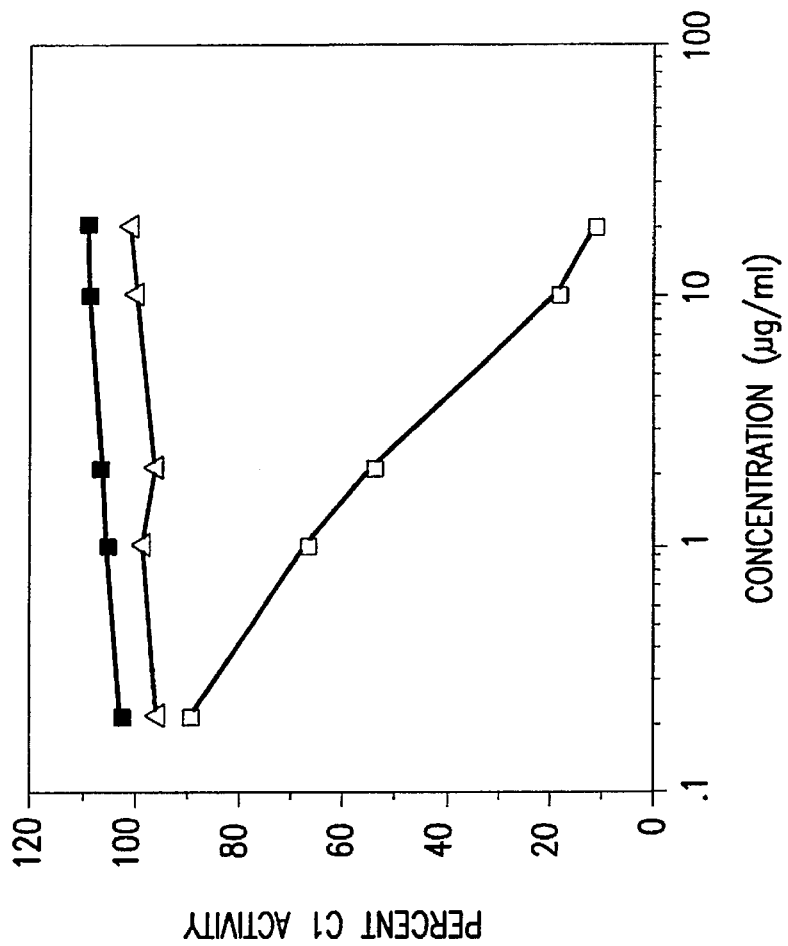

Inhibition of C1 by decorin was determined by preincubating decorin with purified C1 or NHS and measuring residual C1 activity by a hemolytic assay. FIG. 7 demonstrates that decorin produced a dose-dependent inhibition of C1 activity. At a concentration of 2 µg/ml, decorin inhibited C1 activity by approximately 50%. A similar degree of inhibition was observed when decorin was incubated with NHS as the source of C1. FIG. 7 also shows that neither the purified core protein, nor the isolated GAG chains of decorin inhibited C1 indicating that the intact proteoglycan is necessary for functional activity.

The inventors also investigated whether decorin would inhibit C1 bound to EAC4 cells. C1 was bound to the surface of EAC4 cells according to the method of Borsos and Rapp (69) included herein as reference. Briefly, EAC4 cells at a concentration of $1.5 \times 10^8$ cells/ml in DGVB$^{++}$ were incubated with an equal volume of purified C1 (diluted to an activity of 1 unit/ml) for 30 min at 30° C. Cells then were pelleted by centrifugation, washed twice with DGVB$^{++}$ and resuspended at a concentration of $1.5 \times 10^8$ cells/ml in the same buffer. Subsequently, the EAC4 cells were incubated with increasing concentrations of decorin or BSA (concentration range 0–20 µg/ml) for 1 h at 0° C. and residual C1 activity was measured as described above. Under these conditions decorin did not inhibit the hemolytic activity of C1.

H. Inhibition of C1q-mediated Superoxide Production in Neutrophils by Decorin

Figure 8:
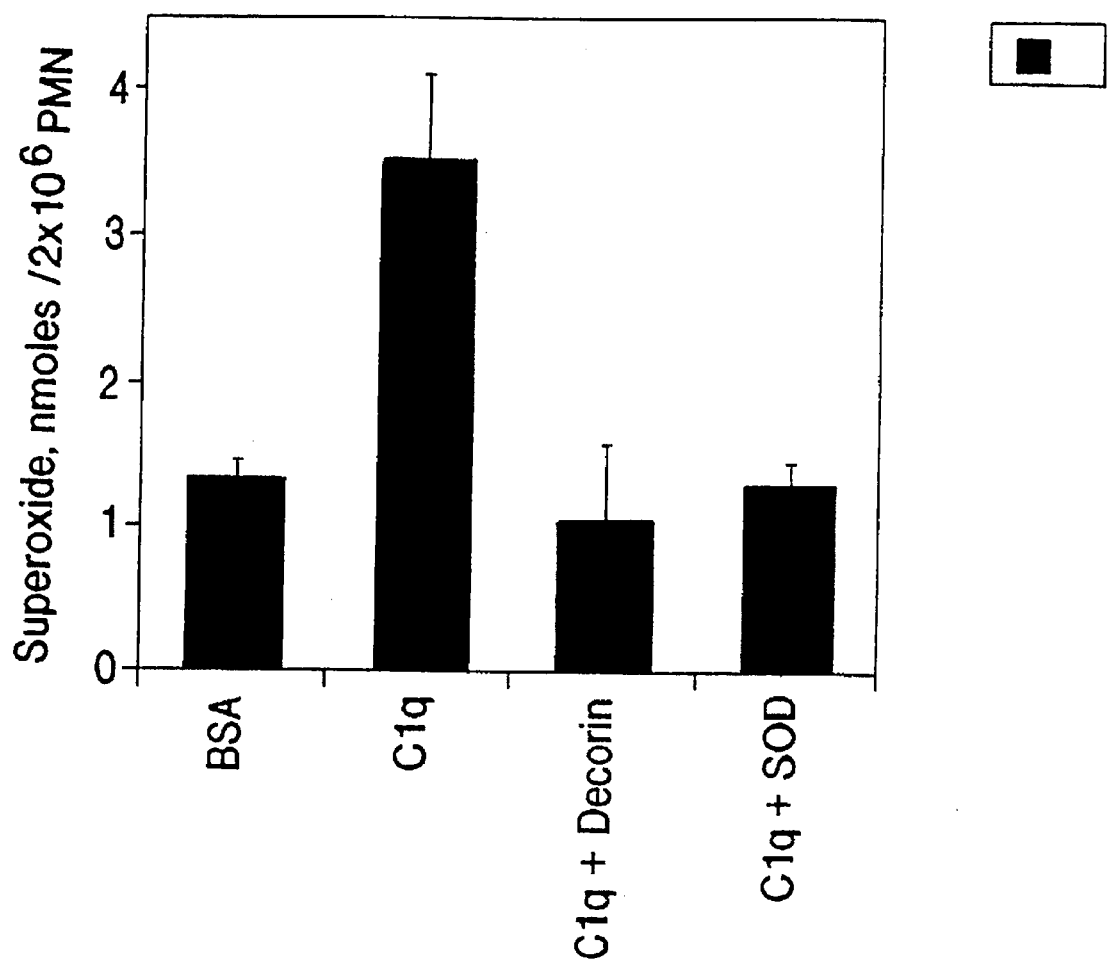
FIG. 8 shows that C1q immobilized on microtiter wells stimulates neutrophil superoxide production when compared to wells coated with BSA.
Figure 9:
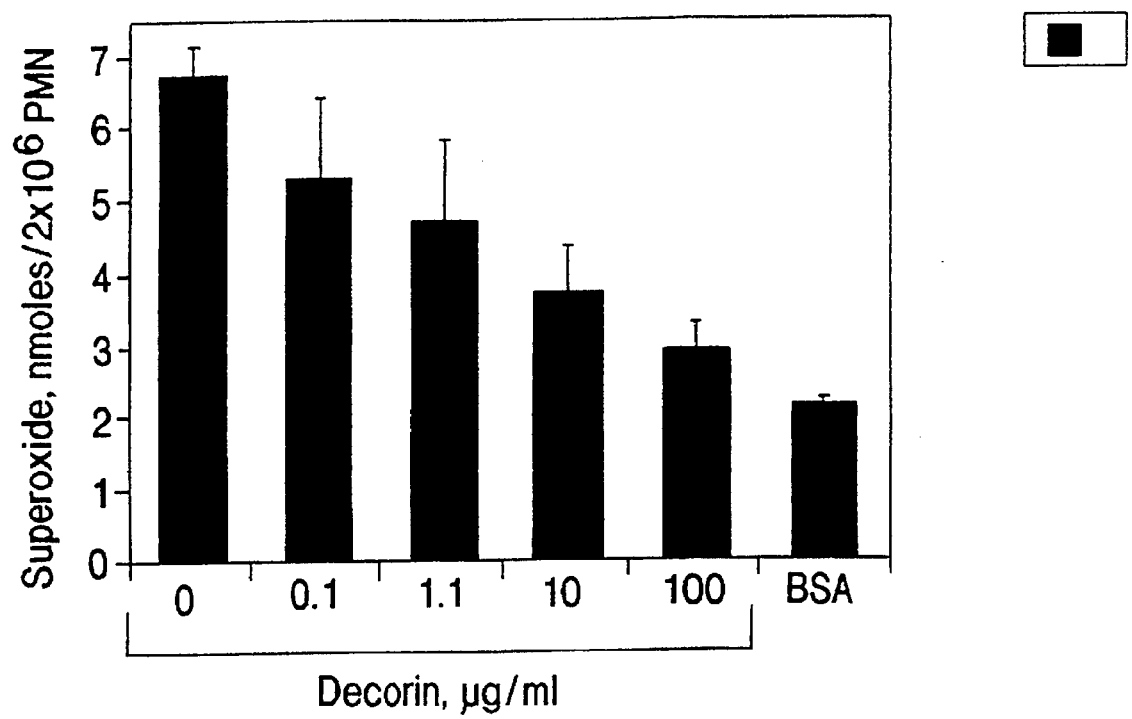
FIG. 9 shows that the inhibition of C1q-mediated superoxide production by decorin is concentration-dependent over a range of 0–100 mg/ml. Superoxide production by neutrophils was measured in response to C1q coated wells containing incremental concentrations of decorin in fluid phase and also in BSA coated wells.

The inventors have recently demonstrated in preliminary studies that decorin inhibits C1q-mediated superoxide production by neutrophils. The production of superoxide by neutrophils in response to plastic wells coated with C1q was quantitated by measuring the superoxide dismutase-inhibitable reduction of cytochrome-C as described by Mayo and Curnutte (71). FIG. 8 shows that C1q immobilized on microtiter wells stimulates neutrophil superoxide production when compared to wells coated with BSA. FIG. 8 further shows that superoxide production is inhibited in wells containing decorin at a concentration of 100 mg/ml, and that the degree of inhibition is equal to that observed in wells containing superoxide dismutase at the same concentration. FIG. 9 shows that the inhibition of C1q-mediated superoxide production by decorin is concentration-dependent over a range of 0–100 mg/ml. Further studies are required to determine the specificity and mechanism of inhibition.

EXAMPLE II

Determining the Mechanism by which Decorin Inhibits the Activity of the Classical Pathway of Complement Activation a. Experimental Design The inventors preliminary studies have demonstrated that decorin inhibits the hemolytic activity of C1 when C1 is in solution, but not when C1 is bound to EAC4 cells, suggesting either that decorin inhibits C1 by preventing binding of C1 to immune complexes, or by binding and dissociating the C1 complex (see sections d and e of preliminary studies for detailed discussion). Further studies showed that decorin does not inhibit binding of C1q to immune complexes. Thus, it is proposed that decorin inhibits activation of the classical complement pathway by binding and dissociating the C1 complex. Furthermore, since decorin does not inhibit C1 bound to EAC4 cells, this implies that decorin dissociates C1 in solution, but not C1 bound to immune complexes. The studies outlined below will test these hypotheses.

To determine whether decorin dissociates C1 in solution, purified C1 will be incubated at room temperature with solutions containing incremental concentrations of decorin in phosphate-buffered saline (PBS). Since C1q exist as a $Ca^{2+}$-dependent complex with C1r and C1s, the phosphate buffers used in these studies will contain 0.15 mM $CaCl_2$. The C1-decorin mixtures will be analyzed by ultracentrifugation on linear sucrose-density gradients and the fractions obtained from these gradients will be assayed for C1q, C1r, C1s, and decorin by enzyme-linked immunosorbent assay (ELISA). As a positive control, C1 will be incubated in phosphate buffer containing 10 mM EDTA. Since the integrity of the C1 complex depends on the presence of calcium ions, the EDTA should dissociate the complex. As a negative control C1 will be incubated with buffer alone. The inventors anticipate that if decorin dissociates C1, subcomponents C1r and C1s either will be released separately with sedimentation coefficients of 6.7–7.0 S (72,73) and 4.3–4.5 S (72,74), respectively; or as a $Ca^{2+}$-dependent tetrameric complex ($C1r_2$ C1s2) with a sedimentation coefficient of 8.7 S (72). On the other hand, if decorin does not dissociate C1, then the inventors expect the intact complex to sediment at a significantly greater velocity.

If the above experiment demonstrates that decorin dissociates C1 in solution, the inventors propose to investigate whether decorin dissociates C1 bound to immune complexes. This will be examined by adsorbing C1 to affinity columns containing heat-aggregated IgG covalently bound to SEPHAROSE™-4B. Following adsorption of C1, the columns will be washed with solutions of decorin in low ionic strength $Ca^{2+}$-containing PBS and fractions of the eluate will be assayed for the release of C1r and C1s by ELISA. As a negative control, columns will be washed with buffer alone, and as a positive control with buffer containing EDTA. The rationale for using low ionic strength phosphate buffer in this experiment is explained below.

A potential problem with the methodology proposed is that the C1 complex may spontaneously dissociate under the conditions described; however, this is unlikely. Studies have demonstrated that C1 in NHS, or reconstituted from subcomponents C1q, C1r, and C1s, sediments as a single macromolecular complex with a sedimentation coefficient of 15–17 S when ultracentrifuged through sucrose density gradients formed in buffers of physiologic ionic strength containing 0.15 mM $CaCl_2$ (73). Another study showed that C1 adsorbed to SEPHAROSE™ 4B-aggregated IgG affinity columns did not dissociate when the columns were washed with $Ca^{2+}$-containing buffers as long as the buffers were of low ionic strength (m=0.7×physiologic) (32). Thus, the inventors expect that under the conditions described, C1 will remain as an intact complex unless actively dissociated by EDTA, or (if our hypothesis is correct) decorin.

b. Methods (i) Purification of C1—Human C1 will be purified as described by Sim (75). A euglobulin precipitate of citrated serum will be washed with low-ionic strength acetate buffer to remove IgG and albumin, and redissolved in 50 mM sodium acetate, 200 mM NaCl, 5 mM $CaCl_2$, pH 5.5. The redissolved euglobulin then will be fractionated on SEPHAROSE™-6B, equilibrated and eluted with the same buffer. Fractions obtained will be assayed for C1 by a hemolytic assay as described by Borsos and Rapp (1963), and C1-containing fractions will be concentrated by ultrafiltration and analyzed by SDS-PAGE (76).

(ii) Purification of decorin—Decorin will be purified from bovine articular cartilage as described by Choi et al. (77). Briefly, a mixture of decorin (DSPG-II) and biglycan (DSPG-I) will be isolated from cartilage by dissociative extraction with 4M guanidine hydrochloride followed by equilibrium density gradient centrifugation, DEAE-SEPHACEL™ chromatography, and gel chromatography on SEPHAROSE™ CL-4B. DSPG-I and DSPG-II then will be separated by chromatography on octyl-SEPHAROSE™.

(iii) Sucrose-density gradient ultracentrifugation—200 ml samples of purified C1, C1+decorin, or C1+EDTA will be applied to sucrose-density gradients prepared in PBS containing 0.15 mM $CaCl_2$ and centrifuged on a Beckman LB-M Ultracentrifuge. Samples initially will be centrifuged in an SW-50 rotor at 50,000 rpm for 15 h at 4° C. through 9–26 % linear sucrose-density gradients. These conditions were chosen because they have been employed successfully in previous studies on the dissociation of C1 by C1-inhibitor (32). Human C1q (11S), human IgG (7S), serum albumin (4.5S) and horse cytochrome-C (1.7S) will be used to calibrate the gradients (32). Adjustments to optimize the results of our studies will be made as necessary. Following centrifugation, serial fractions will be collected and analyzed for C1q, C1r, C1s, and decorin by ELISA. For the ELISAs, fractions will be coated on plastic microtiter wells and nonspecific binding sites blocked with BSA. Subsequently, rabbit polyclonal IgG against C1q, C1r, C1s, or rabbit polyclonal IgG against bovine decorin will be added followed by the addition of alkaline phosphatase-conjugated goat anti-human IgG. Plates will be developed with p-nitrophenyl phosphate and absorbance at 405 nm measured.

EXAMPLE III

Defining the C1q Binding Site on the Decorin Core Protein by Mutagenesis of the cDNA of Human Decorin a. Experimental Design The inventors' preliminary studies have demonstrated that binding of decorin to C1q is mediated by the decorin core protein. The aim of the studies outlined below is to map the C1q binding site on the decorin core protein and test the hypothesis that binding is mediated by the region of the core protein which contains the tandemly repeated leucine-rich motifs.

To test this hypothesis, deletional mutants of the core protein will be generated by oligonucleotide-directed mutagenesis of the cDNA of human decorin. Full length cDNA clones of human decorin, prepared as described in reference 59, are being provided by Dr. Larry Fisher of the NIH. Since the mature core protein of human decorin consists of 329 amino acids (47), and since the region of the core protein containing the leucine-rich motifs corresponds to amino acid residues 45–279 (48), the inventors will initially work on generating three mutants; one mutant containing a deletion of amino acid residues 1–44 on the amino-terminal side of the leucine-rich domain, a second mutant containing a deletion of amino acid residues 280–329 on the carboxy-terminal side of the leucine-rich domain, and a third mutant containing both deletions. The wild-type and mutant core proteins will be expressed in E. coli as fusion proteins with glutathione-S-transferase (GST) using pGEX vectors.

Following expression, two strategies will be employed to examine their interaction with C1q. First, it is proposed to examine binding of [$^{125}$I] C1q to the fusion proteins immobilized on glutathione-agarose beads. As a positive control for this experiment we will have glutathione-agarose beads containing the wild-type (non-mutated) decorin fusion protein, and as a negative control we will have glutathione-agarose beads containing GST, or glutathione agarose beads alone. The second strategy will examine the competitive inhibition of the binding of [$^{125}$I] decorin to solid-phase C1q by wild-type and mutant core proteins in the fluid phase. For the latter experiments, the GST moiety of the fusion proteins will be removed by proteolytic cleavage with thrombin (if the pGEX-2T vector is employed), or blood coagulation factor Xa (if the pGEX-3X vector is employed).

Further definition of the binding site will depend on the results of the above studies. If, for example, the inventors' studies demonstrate that binding is mediated by the leucine-rich domain, then deletion mutants of this domain will be constructed in order to determine which one(s) and how many of the leucine-rich motifs are necessary for binding. Also, the importance of the leucines contained within the repeating motifs will be examined by constructing mutants where one, or more of the leucines are substituted with other amino acid residues.

b. Methods (i) General Methods

Small-scale plasmid DNA isolation will be carried out by the alkaline lysis method (79). For isolating large quantities of plasmid DNA we will employ the procedure outlined in reference (80). Single and double-stranded M13-derived phage vectors will be isolated as described by Messing (81). Nucleotide sequencing of DNA fragments will be performed by cloning restriction fragments into the complementary filamentous phage vectors M13mp18 and M13mp19 (82) and utilizing the chain-termination method (83). T7 DNA polymerase (84) and buffer gradient gels (85) will be used to resolve the sequencing reaction. To resolve compression bands dITP will be substituted for dGTP (86).

(ii) Production of deletion mutants of decorin cDNA

Deletion mutants will be produced according to the method of Sayers et al. (87) using the oligonucleotide-directed in vitro mutagenesis system of Amersham. This system contains a step where the non-mutant DNA strand is eliminated by specific digestion resulting in a high efficiency of isolation of mutant DNA (see detailed description below).

Wild-type human decorin cDNA will be inserted into the polylinker site of the replicative form of the complementary filamentous phage vectors M13mp18 and M13mp19. Susceptible E. coli strains (JM101 or TG1) made competent by the CaCl$_2$ method (81) will be transformed with these vectors and plated on X-gal agar plates containing isopropyl-1-thio-b-D-galactoside (IPTG). Phage plaques containing the decorin cDNA insert will be identified as white plaques on X-gal agar. Single-stranded vectors from these plaques will be isolated as described (Messing 1983), and the presence and orientation of the inserts will be verified by sequencing. Subsequently, mutagenic oligonucleotides designed to delete appropriate regions of the decorin-cDNA will be annealed to the single stranded template. The mutagenic oligonucleotides employed in these studies will be synthesized in our lab using an Applied Biosystems 394 DNA/RNA synthesizer. These oligonucleotides will be designed such that their sequences contain 12 to 15 complementary bases on each side of the region to be deleted. Furthermore, the choice of the mutagenic oligonucleotides will be optimized for melting temperature and base sequence using the Primer Designer program (Scientific & Educational Software).

After the mutagenic oligonucleotide is annealed to the single stranded template, it will be extended with the Klenow fragment of E. coli DNA polymerase I and ligated with T4-ligase to form a heteroduplex DNA containing a non-mutated parent (+) strand and a mutated (−) strand. Excess single-stranded template then will be removed by filtration through nitrocellulose (87). Extension and ligation of the mutagenic oligonucleotide will be carried out with a deoxynucleotide mixture containing the thionucleotide dCTPaS in place of dCTP. Incorporation of dCTPaS into the newly synthesized (−) strand protects it from cleavage by the frequent-cutting restriction endonuclease Nci-1 (88). This allows the unprotected, non-mutated, (+) strand to be removed by nicking with Nci-1 followed by limited digestion with exonuclease III. The gapped (+) strand then will be repolymerized with DNA polymerase I and ligated with T4 ligase to form a double-stranded homoduplex containing the desired deletion on both strands.

Following formation of the homoduplex, the latter will be used to transform competent E. coli. Single-stranded vector then will be isolated and the insert will be sequenced to confirm the mutation and ensure the absence of unwanted mutations. Subsequently, the double stranded mutant decorin-cDNA will be isolated and subcloned into an appropriate expression vector.

A potential problem with the mutagenic protocol proposed is that because of the homologous repeating leucine-rich segments contained in the decorin core protein, it may be difficult to design mutagenic oligonucleotides that will produce only the desired deletions. However, since the homologies of the leucine-rich segments are not perfect, the Primer Designer Program may find mutagenic oligonucleotides for which the problem of false-priming is acceptably low. If, however, deletion mutants cannot conveniently be prepared by the method proposed, as an alternative, deletion mutants will be obtained using either naturally occurring restriction sites within the wild-type decorin-cDNA, or restriction sites introduced by site-directed mutagenesis.

(iii) Expression of wild-type and mutant cDNA clones

Wild-type and mutant decorin-cDNA clones will be expressed using the pGEX expression system (89), a prokaryotic system which expresses proteins as fusions to the carboxy-terminus of glutathione-S-transferase (GST), a 26 kDa protein originally cloned from *Schistosoma japonicum* (90). The pGEX vectors (FIG. 9) contain a Ptac promoter, the GST coding sequence, a polylinker site containing restriction sites for BamH1, Sma1, and EcoR1; a gene coding for ampicillin resistance, and a fragment of the lac operon encoding the $lacI^q$ allele of the lac repressor. In addition, pGEX vectors 2T and 3X encode within the polylinker for a thrombin cleavage site and a blood coagulation factor Xa cleavage site, respectively. These protease cleavage sites allow for the specific removal of the GST moiety of the fusion proteins. One of the latter two vectors will be employed for expression of wild-type and mutant decorin cDNA clones. The vector chosen will be the one in which the cDNA expressed is in-frame with GST.

Expression of the fusion proteins with these vectors will be performed according to the method of Smith and Johnson (89). Briefly, wild-type and mutant decorin cDNA clones will be subcloned into a pGEX vector. Competent *E. coli* will be transformed and plated on LB/ampicillin plates. As negative controls, some *E. coli* will be transformed with p GEX vectors not containing decorin cDNA inserts. Several transformed colonies will be individually picked, grown in liquid culture, and induced to produce cloned protein with IPTG. The bacteria then will be lysed by sonication and the cell lysates will be screened for the fusion protein by SDS-PAGE developed with Coomasie stain. If the fusion protein is present, transformed colonies will be grown in large scale and the fusion proteins will be purified from cell lysates by affinity adsorption on glutathione-agarose beads followed by elution with excess reduced glutathione.

Again, the eluted fusion proteins will be analyzed by SDS-PAGE and protein concentrations will be determined using the Bio-Rad Protein Assay (91). In some experiments the GST moiety of the fusion proteins will be removed by incubation of the fusion proteins (adsorbed to glutathione-agarose beads) with either thrombin (if pGEX 2T is used), or factor Xa (if pGEX 3X is used). Subsequently GST-containing glutathione-agarose beads will be removed by centrifugation.

Two potential problems with this expression system are instability and poor solubility of the fusion proteins. If the fusion proteins are unstable, the inventors propose to circumvent this problem either by adding protease inhibitors to the lysis buffer (e.g., 1% aprotinin and 1 mM phenylmethylsulfonyl fluoride (PMSF)), or using a protease deficient *E. coli* strain such as the lon$^{(-)}$ strain. If solubility of the fusion protein is a problem, we will attempt to circumvent this by growing the cells at various temperatures, and adding mild detergent to the cell lysates (e.g. 1% Tween-20, 1% Triton X-100). However, if these measures are unsuccessful, it may be necessary to use a eukaryotic expression system which may be more likely to promote proper folding of the expressed protein and enhance solubility. Our lab has extensive experience with the transient expression of proteins in COS cells using the p91023(B) expression vector (92,93, 94). More recently the lab has begun using pCMV expression vectors (95) both for transient expression in COS cells and for the generation of stable transfectants using CHO cells.

(iv) Analysis of the interaction of expressed decorin core proteins with C1q

Two strategies will be employed to analyze the interaction of cloned wild-type and mutant decorin core proteins with C1q. The first strategy will examine the binding of $[^{125}I]$ C1q to the fusion proteins adsorbed on glutathione-agarose beads. Briefly, 25–50 ml of a 50% slurry of glutathione-agarose beads in PBS will be incubated with equimolar amounts of either wild-type, or mutant decorin-GST fusion proteins for 10–20 min at room temperature. Unbound fusion proteins will be removed by washing with cold PBS. Subsequently, incremental amounts of $[^{125}I]$ C1q will be added to the fusion protein-containing beads and the mixtures will be incubated at 37° C. for 1–2 h. Unbound radiolabeled C1q will be removed by washing with PBS containing 0.1% Triton X-100, and bound radiolabeled C1q will be quantitated in a gamma counter. Glutathione-agarose beads containing adsorbed non-mutated decorin fusion protein will be used as a positive control, and glutathione-agarose beads alone, or containing bound GST will be used as negative controls.

Since the GST moiety of the fusion proteins may bind C1q, or change the binding properties of the cloned decorin protein to which it is attached. The second strategy will examine the competitive inhibition of the binding of $[^{125}I]$ decorin to solid-phase C1q by wild-type or mutant decorin core proteins from which the GST moieties have been removed by proteolytic cleavage. In these studies, $[^{125}I]$ decorin (150,000 cpm) will be mixed with incremental concentrations of wild-type, or mutant decorin core protein. The mixtures will be added to microtiter wells coated with C1q and incubated at 37° C. for 1–2 h. Following incubation, unbound material will be removed by washing wells with PBS containing 0.1% Triton X-100 and bound radioactivity will be quantitated in a gamma counter. As a negative control, some wells will contain BSA as a competitive inhibitor, and as a positive control other wells will have unlabeled intact decorin (purified from bovine cartilage), or the native core protein (obtained by digestion of the bovine decorin with chondroitinase-ABC) as inhibitors.

EXAMPLE IV

The Mechanism and Specificity of Decorin Inhibition of C1q-mediated Oxidative Burst by Neutrophils a. Experimental Design Preliminary data from the inventors' lab demonstrate that fluid-phase decorin produces a dose-dependent inhibition of C1q-mediated superoxide production by human neutrophils. In order to determine the specificity of this inhibition, the inventors propose to examine the effect of increasing concentrations of fluid-phase decorin on the production of superoxide by neutrophils exposed to C1q-coated microtiter wells. This study will include other C1q-binding proteins such as C-reactive protein, fibronectin and fibrinogen, as controls. [IgG was not selected as a control because it binds Fc receptors on neutrophils and stimulates superoxide production (96)]. Having these controls will tell us whether inhibition of C1q-mediated superoxide production is specific for decorin, or a general feature of C1q-binding proteins.

In addition, the inventors propose to examine the effect of fluid-phase decorin on neutrophil superoxide production in response to other agonists such as phorbol 12-myristate 13-acetate (PMA), the chemotactic peptide FMLP, and soluble BSA anti-BSA complexes. This experiment will determine if decorin specifically inhibits C1q-mediated superoxide production, or inhibits C1q production in response to other agonists as well.

Assuming that these studies will confirm that decorin specifically inhibits C1q-mediated superoxide production, then inventors will test the possibility that the mechanism by which decorin interferes with neutrophil superoxide production is by competitive inhibition of the binding of C1q to its receptor on the cell surface of neutrophils. This hypothesis will be tested by measuring the binding of $^{125}$I-labeled monomeric C1q to neutrophils in the presence of increasing concentrations of decorin. In these studies, BSA will be used as a negative control and excess unlabeled C1q as a positive control.

A potential problem with the experiments outlined above is that binding of monomeric C1q to neutrophils may be difficult to quantitate. This is suggested by the observation that monomeric C1q in solution does not stimulate neutrophil oxidative burst (38). The latter may reflect a requirement for multivalency of the C1q ligand for optimal binding to the neutrophil receptor. In fact, Tenner and Cooper reported that only 0–5% of circulating neutrophils could be shown to bind monomeric C1q as determined by immunofluorescent microscopy; however, binding was enhanced significantly in buffers of low ionic strength (m=0.09) (33). Accordingly, binding assays will be done in phosphate buffers having an ionic strength of 0.09.

b. Methods (i) General Methods

C1q will be purified from human plasma according to the method of Tenner et al. (97). Briefly, fresh frozen plasma made 5 mM in EDTA will be applied to a BioRex column (previously equilibrated with 50 mM phosphate buffer containing 82 mM NaCl, 2 mM EDTA, pH7.3) and eluted with a NaCl gradient (82–300 mM).

Fractions containing C1q will be detected by Ouchterlony immunodiffusion using rabbit anti-C1q antisera (available in our lab). C1q-containing fractions will be pooled and precipitated at 33% ammonium sulfate and redissolved in 500 mM NaCl, 50 mM Tris, 2 mM EDTA pH7.2. The redissolved precipitate will be fractionated on Biogel A5M and C1q containing fractions will be pooled and analyzed for purity by SDS-PAGE. C1q protein concentrations will be determined by measuring absorbance at 280 nm using an extinction coefficient (E=6.82) (67). C1q will be radiolabeled with Na$^{125}$I using ENZYMOBEADS™ (Bio-Rad Laboratories) according to the manufacturer's instructions.

Human neutrophils will be prepared from acid-citrate dextrose anticoagulated blood by dextran sedimentation of erythrocytes, Ficoll-Hypaque density gradient centrifugation to separate mononuclear cells from neutrophils, and hypotonic lysis of residual red cells as described (98).

(ii) Measurement of superoxide production

IMMULON™-2 microtiter wells will be coated with C1q (100–300 mg/ml) diluted in 0.1M carbonate buffer, pH9.0 and nonspecific binding sites will be blocked with BSA. C1q-mediated superoxide production then will be measured by the superoxide dismutase inhibitable reduction of cytochrome-C as adapted to a microplate format by Mayo and Curnutte (71). Briefly, a reaction mixture will be prepared containing cytochrome-C (100 mM), increasing concentrations of decorin or a control protein, and $1-2\times10^6$ neutrophils/ml diluted in Hank's balanced salt solution containing calcium, magnesium, and 1 mg/ml glucose. This reaction mixture will be added to the C1q-coated wells and the change in absorbance at 550 nm will be monitored over time.

To obtain nanomoles $O_2$, the initial absorbance will be subtracted from the final absorbance and this value will be converted to nanomoles $O_2$ using the extinction coefficient 0.022 mM$^{-1}$ cm$^{-1}$ (39). Control wells containing superoxide dismutase will be run in parallel. In addition, in some experiments soluble agonist such as FMLP at $5\times10^{-7}$M, PMA at 25 ng/ml, or BSA anti-BSA complexes will substitute for solid-phase C1q.

(iii) Detection of [$^{125}$I] C1q-binding to neutrophils

Binding of [$^{125}$I] C1q to neutrophils will be measured as described (33). Mixtures of $10^6$ neutrophils with solutions of [$^{125}$I] C1q and either increasing concentrations of decorin, or BSA in a low ionic strength (m=0.09) phosphate buffer will be incubated on ice for 15–30 min. Subsequently, bound and unbound [$^{125}$I] C1q will be separated by centrifugation through a 4:1 (v/v) mixture of n-butyl- phthalate and bis (2-ethylhexyl) phthalate. The tip of the tube containing the cell pellet will be cut and the pellet and remaining tube contents will be counted separately in a gamma counter.

(iv) Preparation of BSA anti-BSA complexes

BSA anti-BSA complexes will be prepared at equivalence by mixing equal volumes of BSA (200 mg/ml) and heat inactivated rabbit anti-BSA serum as previously described (99).

EXAMPLE V

Assessing the Biological Action of Structurally Related Proteoglycans a. Experimental Design Decorin belongs to a family of structurally related matrix proteoglycans which have as common features a broad tissue distribution and tandemly repeated leucine-rich motifs which comprise the majority of the primary structures of their core proteins. These proteoglycans include biglycan (49), lumican (50,100), and fibromodulin (51). The inventors propose that, some of these structurally related proteoglycans also may modulate complement activity. Specifically, the inventors propose to examine whether other members of the decorin family such as biglycan and lumican bind C1q and modulate C1 activity.

Binding of biglycan and lumican to C1q will be examined by a radioactive solid-phase binding assay following the general strategy and methodology employed to demonstrate binding of decorin to C1q (see Example I). If either biglycan, or lumican binds C1q, then we will proceed to further characterize the interaction. To determine if the interaction is saturable, increasing amounts of radiolabeled proteoglycan of known specific activity will be added to plastic wells coated with C1q, or as a measure of non-specific binding, BSA. Following incubation, unbound material will be removed by washing, and bound and unbound radioactivity will be quantitated. Specific binding will be calculated as the amount of proteoglycan bound to C1q minus that bound to BSA.

If the reaction is saturable, a Scatchard plot of the data and the dissociation constant can be calculated as the negative reciprocal of the slope of the line of the Scatchard plot (101). To determine if binding is mediated by the proteoglycan core protein or the glycosaminoglycan (GAG) chains, the intact proteoglycan, its core protein and GAG chains can be tested as competitive inhibitors of the binding of radiolabeled proteoglycan to C1q. To localize the proteoglycan binding site of C1q, proteolytic fragments of the collagenous and globular domains of C1q will be tested as competitive inhibitors of the binding of radiolabeled proteoglycan to C1q.

Lastly, if either of the two proteoglycans bind C1q, we will examine whether they activate or inhibit C1. Activation of C1 will be determined indirectly by measuring C4 consumption following incubation of normal human serum (NHS) with increasing concentrations of the proteoglycan or as a positive control, BSA anti-BSA complexes. Inhibition of C1 will be examined by incubating the proteoglycan with purified C1 or C1 in NHS, and measuring residual C1 activity by a hemolytic assay. Again, the studies can be carried out as described in Example I.

b. Methods

C1q will be purified from human plasma as described previously. Proteolytic fragments of C1q containing the collagenous domain will be prepared by limited digestion of intact C1q with pepsin according to the method of Reid and Porter (66), and fragments containing the globular domain will be prepared by digestion of C1q with collagenase according to the method of Reid and Edmondson (67). Following digestion with pepsin, or collagenase, the C1q fragments will be purified by FPLC on a Superose-12 column as described by Jiang et al. (102). Bovine biglycan will be purified as previously described (see specific aim #1). Lumican, purified from bovine aorta, will be provided by Dr. James L. Funderburgh.

Core protein preparations of the proteoglycans will be obtained by digesting the intact proteoglycans with chondroitinase ABC (0.2 units/mg protein) and the core proteins will be purified by FPLC on a Mono-Q column as described (103). Binding of radiolabeled proteoglycan to solid-phase C1q, or of radiolabeled C1q to solid-phase proteoglycan will be performed exactly as described in the inventors' manuscript (103). Briefly, IMMULON™-2 microtiter wells will be coated with C1q in PBS (10 mg/ml) overnight at 4° C. Nonspecific binding sites will be blocked with 1% BSA followed by the addition of $5 \times 10^4$ cpm of $^{125}$I-labeled proteoglycan in PBS. The mixtures will be incubated at 37° C. for 1–2 hours. Following incubation unbound material will be removed by washing with PBS containing 0.1% Triton X-100 and bound material will be quantitated in a gamma counter. In some experiments, wells will be coated with proteoglycan and radiolabeled C1q will be added.

C4 consumption assay will be performed by incubating aliquots of NHS with increasing concentrations of proteoglycan and measuring residual C4 activity according to the method of Gaither (68). Hemolytic units will be calculated as described (104). C1 fixation assays will be performed by incubating aliquots of purified C1 or C1 in NHS (diluted to a C1 activity of 1 unit/ml in low ionic strength veronal buffered saline) with increasing concentrations of proteoglycan, and measuring residual C1 activity as described by Borsos and Rapp (69).

EXAMPLE VI

This example presents a preferred method for the preparation of a pharmacologically acceptable composition for the clinical administration of decorin. Recombinant human decorin for parenteral administration to human subjects may be isolated from the conditioned media of a chinese hamster ovary cell line that overexpresses human decorin as a result of DNA transfection and subsequent gene amplification (59). The human decorin can be purified by ion exchange on DEAE-SEPHACEL™ and octyl-SEPHAROSE™ as described by Choi et. al. (77). Following elution and dialysis against distilled water, the recombinant decorin may be lyophilized and stored at 4° C. for future use. Lyophiized decorin retains complement inhibitory activity for several months. Prior to parenteral administration human decorin can be reconstituted in a small volume of distilled water, $d_5W$, normal saline or other suitable physiologic buffer to a concentration of 5 mg/ml.

EXAMPLE VII

In the clinical setting, decorin may be administered in several disease states where complement has been demonstrated to participate in the pathogenesis of host tissue damage. These diseases included myocardial infarction, burn injury and autoimmune diseases such as systemic lupus erythematosus. Base on the foregoing discussion regarding preparation of recombinant pharmaceutical compositions of decorin, and assuming an in vivo one-half life of about 24 hours, recombinant human decorin would be administered to a patient in need at a concentration of 5 mg/ml as an intravenous bolus injection at a dose of about 4.5 to 7.5 mg/day (about 1.5 to 3.5 mls/day). It is proposed that such a dosage would result in therapeutic plasma concentrations of about 2 to about 5 µg/ml.

As an example, a patient with systemic lupus with active disease manifested by one or more disease parameters such as arthralgias, serositis, skin rash, deteriorating renal function, and systemic complement activation would be treated with parenteral decorin in the doses mentioned above and monitored for subjective improvement of symptoms and objective improvement as determined by measurements such as the extent of skin rash, range of joint movement, serum creatinine and 24-hour urine protein, and total hemolytic complement activity (CH50). Decorin may be administered in other disease settings in a similar fashion.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Miller-Eberhard, H. J. 1988. Molecular organization and function of the complement system. Ann. Rev. Biochem., 57:321–347.
2. Volanakis, J. E. and D. T. Fearon. 1992. The molecular biology of the complement system. In: *Arthritis & Allied Conditions*, 12th edition, (D. J. McCarty and W. J. Koopman, eds.).
3. Hugli, T. E. and H. J. Miller-Eberhard. 1978. Anaphylatoxins: C3a and C5a. In: *Advances in Immunology*, vol. 26, Academic Press, 1–48.
4. Okusawa, S., K. B. Yancey, J. W. M. van der Meer, S. Endres, G. Lonnemann, K. Hefter, M. M. Frank, J. F. Burke, C. A. Dinarello, and J. A. Gelfand. 1988. C5a stimulates secretion of tumor necrosis factor from human mononuclear cells in vitro: Comparison with secretion of interleukin 1b and interleukin 1a. J. Exp. Med. 168:443–448.

5. Wright, S. D. and S. C. Silverstein. 1983. Receptors for C3b and C3bi promote phagocytosis but not the release of toxic oxygen from human phagocytes. J. Exp. Med. 158:2016–2023.
6. Miller-Eberhard, H. J. 1986. The membrane attack complex of complement. Annu. Rev. Immunol. 4:503–528.
7. Colten, H. R. and F. S. Rosen. 1992. Complement deficiencies. Annu. Rev. Immunol. 10:809–834.
8. Morgan, K., R. B. Clague, M. J. Shaw, S. A. Firth, T. M. Twose, and P. J. L. Holt. 1981. Native type II collagen-induced arthritis in the rat. Arthritis Rheum. 24:1356–1361.
9. Watson, W. C., P. S. Brown, J. A. Pitcock, and A. S. Townes. 1987. Passive transfer studies with type II collagen antibody in B10.D2/old and new line and C57B1/6 normal and beige (Chediak-Higashi) strains: Evidence of important roles for C5 and multiple inflammatory cell types in the development of erosive arthritis. Arthritis Rheum. 30:460–465.
10. Lennon, V. A., M. E. Seybold, J. M. Lindstrom, C. Cochrane, and R. Ulevitch. 1978. Role of complement in the pathogenesis of experimental autoimmune myasthenia gravis. J. Exp. Med. 147:973–983.
11. Biesecker, G. and C. M. Gomez. 1989. Inhibition of acute passive transfer experimental autoimmune myasthenia gravis with Fab antibody to complement C6. J. Immunol. 142:2654–2659.
12. Salant, D. J., S. Belok, M. P. Madaio, and W. G. Couser. 1980. A new role for complement in experimental membranous nephropathy in rats. J. Clin. Invest. 66:1339–1350.
13. Groggel, G. C., S. Adler, H. G. Rennke, W. G. Couser, and D. J. Salant. 1983. Role of the terminal complement pathway in experimental membranous nephropathy in the rabbit. J. Clin. Invest. 72:1948–1957.
14. Maroko, P. R., C. B. Carpenter, M. Chiariello, M. C. Fishbein, P. Radvany, J. D. Knostman, and S. L. Hale. 1978. Reduction by cobra venom factor of myocardial necrosis after coronary artery occlusion. J. Clin. Invest. 61:661–670.
15. Weisman, H. F., T. Bartow, M. K. Leppo, H. C. Marsh, Jr., G. R. Carson, M. F. Concino, M. P. Boyle, K. H. Roux, M. L. Weisfeldt, and D. T. Fearon. 1990. Soluble human complement receptor type 1: in vivo inhibitor of complement suppressing post-ischemic myocardial inflammation and necrosis. Science 249:146–151.
16. Gelfand, J. A., M. Donelan, A. Hawiger, and J. F. Burke. 1982. Alternative complement pathway activation increases mortality in a model of burn injury in mice. J. Clin. Invest. 70:1170–1176.
17. Mulligan, M. S., C. G. Yeh, A. R. Rudolph, and P. A. Ward. 1992. Protective effects of soluble CR1 in complement- and neutrophil-mediated tissue injury. J. Immunol. 148:1479–1485.
18. Liszewski, M. K., T. W. Post, and J. P. Atkinson. 1991. Membrane cofactor protein (MCP OR CD46): Newest member of the regulators of complement activation gene cluster. Annu. Rev. Immunol. 9:431–455.
19. Oglesby, T. J., C. J. Allen, M. A. Liszewski, D. J. G. White, and J. P. Atkinson. 1992. Membrane cofactor protein (CD46) protects cells from complement-mediated attack by an intrinsic mechanism. J. Exp. Med. 175:1547–1551.
20. Lublin, D. M. and J. P. Atkinson. 1989. Decay-accelerating factor: biochemistry, molecular biology, and function. Annu. Rev. Immunol. 7:35–58.
21. Holguin, M. H., L. R. Fredrick, N. J. Bernshaw, L. A. Wilcox, and C. J. Parker. 1989. Isolation and characterization of a membrane protein from normal human erythrocytes that inhibits reactive lysis of the erythrocytes of paroxysmal nocturnal hemoglobinuria. J. Clin. Invest. 84:7–17.
22. Zalman, L. S., L. M. Wood, and H. J. Miller-Eberhard. 1986. Isolation of a human erythrocyte membrane protein capable of inhibiting expression of homologous complement transmembrane channels. Proc. Natl. Acad. Sci. U.S.A. 83:6975–6979.
23. Doering, T. L., W. J. Masterson, G. W. Hart, and P. T. Englund. 1990. Biosynthesis of glycosyl phosphatidylinositol membrane anchors. J. Biol. Chem. 265:611–614.
24. Rosse, W. F. 1990. Phosphatidylinositol-linked proteins and paroxysmal nocturnal hemoglobinuria. Blood 75:1595–1601.
25. Cooper, N. R. 1985. The classical complement pathway: activation and regulation of the first complement component. Adv. Immunol. 37:151–216.
26. Reid, K. B. M. 1989. C1q: Genes, biosynthesis and biology. Behring Inst. Mitt. 84:8–19.
27. Shelton, E., K. Yonemasu, and R. M. Stroud. 1972. Ultrastructure of the human complement component, C1q. Proc. Natl. Acad. Sci. U.S.A. 69:65–68.
28. Reid, K. B. M., R. B. Sim and A. P. Faiers. 1977. Inhibition of the reconstitution of the haemolytic activity of the first component of human complement by a pepsin-derived fragment of subcomponent C1q. Biochem. J. 161:239–245.
29. Strang, C. J., R. C. Siegel, M. L. Phillips, P. H. Poon, and V. N. Schumaker. 1982. Ultrastructure of the first component of human complement: electron microscopy of the crosslinked complex. Proc. Natl. Acad. Sci. U.S.A. 79:586–590.
30. Hughes-Jones, N. C. and B. Gardner. 1979. Reaction between the isolated globular sub-units of the complement component C1q and IgG-complexes. Mol. Immunol. 16:697–701.
31. Schumaker, V. N., P. Zavodszky, and P. H. Poon. 1987. Activation of the first component of complement. Annu. Rev. Immunol. 5:21–42.
32. Ziccardi, R. J. and N. R. Cooper. 1979. Active disassembly of the first complement component J. Immunol. 123:788–792.
33. Tenner, A. J. and N. R. Cooper. 1981. Identification of types of cells in human peripheral blood that bind C1q. J. Immunol. 126:1174–1179.
34. Bordin, S., W. P. Kolb and R. C. Page. 1983. C1q receptors on cultured human gingival fibroblasts: analysis of binding properties. J. Immunol. 130:1871–1875.
35. Bobak, D. A., T. A. Gaither, M. M. Frank and A. J. Tenner. 1987. Modulation of FcR function by complement: subcomponent C1q enhances the phagocytosis of IgG-opsonized targets by human monocytes and culture-derived macrophages. J. Immunol. 138:1150–1156.
36. Young, K. R., Jr., J. L. Ambrus, Jr., A. Malbran, A. S. Fauci and A. J. Tenner. 1991. Complement subcomponent C1q stimulates Ig production by human B lymphocytes. J. Immunol. 146:3356–3364.
37. Oiki, S. and Y. Okada. 1988. C1q induces chemotaxis and $K^+$ conductance activation coupled to increased cytosolic $Ca^{2+}$ in mouse fibroblasts. J. Immunol. 141:3177–3185.
38. Tenner, A. J. and N. R. Cooper. 1982. Stimulation of a human polymorphonuclear leukocyte oxidative response by the C1q subunit of the first complement component. J. Immunol. 128:2547–2552.
39. Goodman, E. B. and A. J. Tenner. 1992. Signal transduction mechanisms of C1q-mediated superoxide production: Evidence for the involvement of temporally distinct staurosporine-insensitive and -sensitive pathways. J. Immunol. 148:3920–3928.
40. Bing, D. H., S. Almeda, H. Isliker, J. Lahav and R. O. Hynes. 1982. Fibronectin binds to the C1q component of complement. Proc. Natl. Acad. Sci. U.S.A. 79:4198–4201.
41. Ingham, K. C., R. Landwehr and J. Engel. 1985. Interaction of fibronectin with C1q and collagen. Eur. J. Biochem. 148:219–224.
42. Bohnsack, J. F., A. J. Tenner, G. W. Laurie, H. K. Kleinman, G. R. Martin and E. J. Brown. 1985. The C1q subunit of the first component of complement binds to laminin: A mechanism for the deposition and retention of immune complexes in basement membrane. Proc. Natl. Acad. Sci. U.S.A. 82:3824–3828.
43. Entwistle, R. A. and L. T. Furcht. 1988. C1q component of complement binds to fibrinogen and fibrin. Biochemistry 27:507–512.
44. Poole, A. R., C. Webber, I. Pidoux, H. Choi and L. C. Rosenberg. 1986. Localization of a dermatan sulfate proteoglycan (DS-PGII) in cartilage and the presence of an immunologically related species in other tissues. J. Histochem. Cytochem. 34:619–625.
45. Lennon, D. P., D. A. Carrino, M. A. Baber and A. I. Caplan. 1991. Generation of a monoclonal antibody against avian small dermatan sulfate proteoglycan: Immunolocalization and tissue distribution of PG-II (decorin) in embryonic tissues. Matrix 11:412–427.
46. Rosenberg, L. C., H. U. Choi, L-H Tang, T. L. Johnson, S. Pal, C. Webber, A. Reiner and R. Poole. 1985. Isolation of dermatan sulfate proteoglycans from mature bovine articular cartilages. J. Biol. Chem. 260:6304–6313.
47. Krusius, T. and E. Ruoslahti. 1986. Primary structure of an extracellular matrix proteoglycan core protein deduced from cloned cDNA. Proc. Natl. Acad. Sci. U.S.A. 83:7683–7687.
48. Patthy, L. 1987. Detecting homology of distantly related proteins with consensus sequences. J. Mol. Biol. 198:567–577.
49. Fisher, L. W., J. D. Termine and M. F. Young. 1989. Deduced protein sequence of bone small proteoglycan I (biglycan) shows homology with proteoglycan II (decorin) and several nonconnective tissue proteins in a variety of species. J. Biol. Chem. 264:4571–4576.
50. Blochberger, T. C., J-P Vergnes, J. Hempel and J. R. Hassell. 1992. cDNA to chick lumican (corneal keratan sulfate proteoglycan) reveals homology to the small interstitial proteoglycan gene family and expression in muscle and intestine. J. Biol. Chem. 267:347–352.
51. Oldberg, A. P. Antonsson, K. Lindblom and D. Heinegard. 1989. A collagen-binding 59-kd protein (fibromodulin) is structurally related to the small interstitial proteoglycans PG-S1 and PG-S2 (decorin). EMBO J. 8:2601–2604.
52. Takahashi, N., Y. Takahashi and F. W. Putnam. 1985. Periodicity of leucine and tandem repetition of a 24-amino acid segment in the primary structure of leucine-rich $a_2$-glycoprotein of human serum. Proc. Natl. Acad. Sci. U.S.A. 82:1906–1910.
53. Titani, K., K. Takio, M. Handa and Z. M. Ruggeri. 1987. Amino acid sequence of the von Willebrand factor-binding domain of platelet membrane glycoprotein Ib. Proc. Natl. Acad. Sci. U.S.A. 84:5610–5614.
54. Kataoka, T., D. Broek and M. Wigler. 1985. DNA sequence and characterization of the S. cerevisiae gene encoding adenylate cyclase. Cell 43:493–505.
55. Reinke, R., D. E. Krantz, D. Yen and S. L. Zipursky. 1988. Chaoptin, a cell surface glycoprotein required for drosophila photoreceptor cell morphogenesis, contains a repeat motif found in yeast and human. Cell 52:291–301.
56. Hashimoto, C, K. L. Hudson and K. V. Anderson. 1988. The Toll gene of drosophila, required for dorsal-ventral embryonic polarity, appears to encode a transmembrane protein. Cell 52:269–279.
57. Suzuki, N., H-R Choe, Y. Nishida, Y. Yamawaki-Kataoka, S. Ohnishi, T. Tamaoki and T. Kataoka. 1990. Leucine-rich repeats and carboxyl terminus are required for interaction of yeast adenylate cyclase with RAS proteins. Proc. Natl. Acad. Sci. U.S.A. 87:8711–8715.
58. Schmidt, G., H. Robenek, B. Harach, J. Glessl, V. Nolte, H. Hormann, H. Richter and H. Kresse. 1987. Interaction of small dermatan sulfate proteoglycan from fibroblasts with fibronectin. J. Cell Biol. 104:1683–1691.
59. Yamaguchi, Y., D. M. Mann and E. Ruoslahti. 1990. Negative regulation of transforming growth factor-b by the proteoglycan decorin. Nature 346:281–284.
60. Brown, D. C. and K. G. Vogel. 1989. Characteristics of the in vitro interaction of a small proteoglycan (PGII) of bovine tendon with type 1 collagen. Matrix 9:468–478.
61. Bidanset, D. J., C. Guidry, L. C. Rosenberg, H. U. Choi, R. Timpl and M. Höök. 1992. Binding of the proteoglycan decorin to collagen type VI. J. Biol. Chem. 267:5250–5256.
62. Lewandowska, K. H. U. Choi, L. C. Rosenberg, L. Zardi and L. A. Culp. 1987. Fibronectin-mediated adhesion of fibroblasts: Inhibition by dermatan sulfate proteoglycan and evidence for a cryptic glycosaminoglycan-binding domain. J. Cell Biol. 105:1443–1454.
63. Vogel, K. G., M. Paulsson and D. Heinegard. 1984. Specific inhibition of type I and type II collagen fibrillogenesis by the small proteoglycan of tendon. Biochem. J. 223:587–597.
64. DeSimone, D. P., D. B. Parsons, K. E. Johnson and R. P. Jacobs. 1983. Type II collagen-induced arthritis—a morphologic and biochemical study of articular cartilage. Arthritis Rheum. 26(10):1245–1258.
65. Stuart, J. M., W. C. Watson and A. H. Kang. 1988. Collagen autoimmunity and arthritis. FASEB J. 2:2950–2956.
66. Reid, K. B. M. and R. R. Porter. 1976. Subunit composition and structure of subcomponent C1q of the first component of human complement. Biochem. J. 155:19–23.
67. Reid, K. B. M. and J. Edmondson. 1984. Location of the binding site in subcomponent C1q for plasma fibronectin. Acta path. microbiol. immunol. scand. Sect. C. Suppl. 284. 92:11–17.
68. Gaither, T. A., D. W. Alling and M. M. Frank. 1974. A new one-step method for the functional assay of the fourth component (C4) of human and guinea pig complement. J. Immunol. 113:574–583.
69. Borsos, T. and H. J. Rapp. 1963. Chromatographic separation of the first component of complement and its assay on a molecular basis. J. Immunol. 91:851–858.
70. Hughes-Jones, N. C. and B. D. Gorick. 1982. The binding and activation of the C1r-C1s subunit of the first component of human complement. Mol. Immunol. 19:1105–1112.
71. Mayo, L. A. and J. T. Curnutte. 1990. Kinetic microplate assay for superoxide producton by neutrophils and other phagocytic cells. Methods Enzymol. 186:567–575.
72. Tschopp, J., W. Villiger, H. Fuchs, D. Kilchherr and J. Engel. 1980. Assembly of subcomponents C1r and C1s of 73. Ziccardi, R. J. and N. R. Cooper. 1977. The subunit composition and sedimentation properties of human C1. J. Immunol. 118:2047–2052.
74. Valet, G. and N. R. Cooper. 1974. Isolation and characterization of the proenzyme form of the C1s subunit of the first complement component. J. Immunol. 112:339–350.
75. Sim, R. B. 1981. The first component of human complement-C1. Methods Enzymol. 80:6–16.
76. Laemmli, U. K. and M. Favre. 1973. Maturation of the head of bacteriophage T4. I. DNA packaging events. J. Mol. Biol. 80:575–599.
77. Choi, H. U., T. L. Johnson, S. Pal, L-H Tang, L. Rosenberg and P. J. Neame. 1989. Characterization of the dermatan sulfate proteoglycans, DS-PGI and DS-PGII, from bovine articular cartilage and skin isolated by octyl-sepharose chromatography. J. Biol. Chem. 264:2876–2884.
78. Krantz, D. D., R. Zidovetzki, B. L. Kagan and S. L. Zipursky. 1991. Amphipathic b structure of a leucine-rich repeat peptide. J. Biol. Chem. 266:16801–16807.
79. Birnboim, H. C. and J. Doly. 1979. A rapid alkaline extraction procedure for screening recombinant plasmid DNA. Nucleic Acids Res. 7:1513–1523.
80. *Current Protocols in Molecular Biology*, vol. 1. 1988. (Ausubel, F. M. et al., editors), John Wiley & Sons, N.Y., 1.7.5–1.7.11.
81. Messing, J. 1983. New M13 vectors for cloning. Methods Enzymol. 101:20–78.
82. Norrander, J., T. Kempe and J. Messing. 1983. Construction of M13 vectors using oligonucleotide-directed mutagenesis. Gene 26:101–107.
83. Sanger, F., S. Nicklen and A. R. Coulson. 1977. DNA sequencing with chain-terminating inhibitors. Proc. Natl. Acad. Sci. U.S.A. 74:5463–5467.
84. Tabor, S. and C. C. Richardson. 1987. DNA sequence analysis with a modified bacteriophage T7 DNA polymerase. Proc. Natl. Acad. Sci. U.S.A. 84:4767–4771.
85. Biggin, M. D., T. J. Gibson and G. F. Hong. 1983. Buffer gradient gels and $^{35}S$ label as an aid to rapid DNA sequence determination. Proc. Natl. Acad. Sci. U.S.A. 80:3963–3965.
86. Mills, D. R. and F. R. Kramer. 1979. Structure-independent nucleotide sequence analysis. Proc. Natl. Acad. Sci. U.S.A. 76:2232–2235.
87. Sayers, J. R., W. Schmidt and F. Eckstein. 1988. 5'-3' Exonucleases in phosphorothioate-based oligonucleotide-directed mutagenesis. Nucleic Acids Res. 16:791–802.
88. Nakamaye, K. L. and F. Eckstein. 1986. Inhibition of restriction endonuclease Nci I cleavage by phosphorothioate groups and its application to oligonucleotide-directed mutagenesis. Nucleic Acids Res. 14: 9679–9698.
89. Smith, D. B. and K. S. Johnson. 1988. Single-step purification of polypeptides expressed in *Escherichia coli* as fusions with glutathione S-transferase. Gene 67:31–40.
90. Smith, D. B, K. M. Davern, P. G. Board, W. U. Tiu, E. G. Garcia and G. F. Mitchell. 1986. Mr 26,000 antigen of *Schistosoma japonicum* recognized by resistant WEHI 129/J mice is a parasite glutathione S-transferase. Proc. Natl. Acad. Sci. U.S.A. 83:8703–8707.
91. Bradford, M. M. 1976. A rapid and sensitive method for the quantitation of microgram quantities of protein utilizing the priciple of protein dye binding. Anal. Biochem. 72:248–254.
92. Horiuchi, T., K. J. Macon, V. J. Kidd and J. E. Volanakis. 1989. cDNA cloning and expression of human complement component C2. J. Immunol. 142:2105–2111.
93. Horiuchi, T., K. J. Macon, J. A. Engler and J. E. Volanakis. 1991. Site-directed mutagenesis of the region around Cys-241 of complement component C2. J. Immunol. 147:584–589.
94. Agrawal, A., Y Xu, D. Ansardi, K. J. Macon and J. E. Volanakis. 1992. Probing the phosphocholine-binding site of human C-reactive protein by site-directed mutagenesis. J. Biol. Chem. (in press).
95. Thomsen, D. R., R. M. Stenberg, W. F. Goins and M. F. Stinski. 1984. Promoter-regulatory region of the immediate early gene of human cytomegalovirus. Proc. Natl. Acad. Sci. U.S.A. 81:659–663.
96. Blackburn, W. D. and L. W. Heck. 1988. Neutrophil activation by surface bound IgG: Pertussis toxin insensitive activation. Biochem. Biophys. Res. Commun. 152:136–142.
97. Tenner, A. J., P. H. Lesavre and N. R. Cooper. 1981. Purification and radiolabeling of human C1q. J. Immunol. 127:648–653.
98. Markert, M., P. C. Andrews and B. M. Babior. 1984. Measurement of $O_2$ production by human neutrophils. The preparation and assay of NADPH oxidase-containing particles from human neutrophils. Method. Enzymol. 105:358–365.
99. Oglesby, T. J., A. Ueda and J. E. Volanakis. 1988. Radioassays for quantitation of intact complement proteins C2 and B in human serum. J. Immunol. Methods. 110:55–62.
100. Funderburgh, J. L., M. L. Funderburgh, M. M. Mann and G. W. Conrad. 1991. Arterial lumican—Properties of a corneal-type sulfate proteoglycan from bovine aorta. J. Biol. Chem. 266(36):24773–24777.
101. Scatchard, G. 1949. The attractions of proteins for small molecules and ions. Ann. N.Y. Acad. Sci. 51:660–672.
102. Jiang, H., J. N. Siegle, and Gewurtz. 1991. Binding and complement activation by C-reactive protein via the collagen-like region of C1q and inhibition of these reactions by monoclonal antibodies to C-reactive protein and C1q. J. Immunol. 146:2324–2330.
103. Krumdieck, R., M. Höök, L. C. Rosenberg and J. E. Volanakis. 1992. The proteoglycan decorin binds C1q and inhibits the activity of the C1 complex. J. Immunol. (in press).
104. Mayer, M. M. 1961. In Experimental Immunochemistry, 2nd Ed. E. Kabat and M. M. Mayer, eds. Charles C. Thomas, Springfield, Ill., chapter 4.
105. Siegel, R. C., and V. N. Schumaker. 1983. Mol. Immunol. 20:53.
106. Goldman, D. and S. A. Sedman. 1981. Science 211:1437.
107. Towbin, H., T. Staehelin, and J. Gordon. 1979. Proc. Natl. Acad. Sci. U.S.A. 76:4350.
108. Scatchard, G. 1949. Ann. N.Y. Acad. Sci. 51:660.
109. Scheinberg, I. H. 1974. Science 185:1184.

What is claimed is:

1. A method for suppressing antibody dependent complement activation in a subject comprising administering to the subject an amount of decorin effective to suppress antibody dependent complement activation in a sterile solution rendered pharmacologically acceptable.

2. A method for inhibiting C1 complex in solution comprising adding to such a solution an amount of decorin that is effective to suppress hemolytic activity of C1.

3. A method for binding decorin to C1q in solution comprising adding to such a solution an amount of decorin that is effective to allow binding of the decorin to the C1q.

4. The method of claim 3, wherein decorin is added as a pharmaceutical composition comprising an effective binding amount of decorin dispersed in an acceptable buffer or stabilizer.

5. The method of claim 4, wherein the pharmaceutical composition is further defined as an aqueous solution comprising from 3 to 7 µg/ml of decorin dispersed in an acceptable buffer or stabilizer.

6. The method of claim 5, wherein the pharmaceutical composition is further defined as comprising an acceptable buffer or stabilizer selected from the group of sterile water, dextrose water, Hank's balanced salt solutions, PBS and Ringer's lactate.

7. The method of claim 3, wherein the decorin is added to the solution to achieve a final concentration of at least about 0.2 to 20 µg/ml.

8. The method of claim 3, wherein the decorin is naturally derived.

9. A method for inhibiting C1' complex activity in solution comprising adding to such a solution an amount of decorin that is effective to suppress hemolytic activity of C1.

10. The method of claim 9, wherein the decorin is added in an amount effective to provide a final concentration of between about 0.2 and about 20 µg/ml.

11. The method of claim 9, wherein decorin is added as a pharmaceutical composition comprising an amount of decorin effective to inhibit C1 complex activity in a sterile solution rendered pharmacologically acceptable.

12. The method of claim 10, wherein the C1 complex is inhibited in human serum at physiological pH.

13. The method of claim 12, wherein the decorin is added in an amount effective to provide a final concentration of between about 0.2 and about 20 µg/ml.

14. A method for reducing the complement activating potential of an implanted medical device comprising coating the implanted medical device with an effective amount of decorin.

15. The method of claim 14, wherein the object comprises medical tubing, a shunt, a catheter or artificial implant.

16. A method for inhibiting C1 complex in a solution having physiological ionic strength, comprising adding to said solution an amount of decorin that is effective to suppress hemolytic activity of C1.

17. The method of claim 16, wherein said decorin is added as a pharmaceutical composition comprising ann amount of decorin effective to suppress hemolytic activity of C1 in a sterile solution rendered pharmacologically acceptable.

18. The method of claim 17, wherein said decorin is added in an amount to achieve a final concentration of between about 0.2 and 20 µg/ml.

19. A method for binding decorin to C1q in a solution of physiological ionic strength, comprising adding to such a solution an amount of decorin that is effective to allow binding of the decorin to the C1q.

20. The method of claim 19, wherein decorin is added as a pharmaceutical composition comprising an effective binding amount of decorin dispersed in an acceptable buffer or stabilizer.

* * * * *